US008317674B2

(12) United States Patent  
Quirico et al.

(10) Patent No.: US 8,317,674 B2
(45) Date of Patent: Nov. 27, 2012

(54) SHIELDING ASSEMBLIES FOR INFUSION SYSTEMS

(75) Inventors: Charles R. Quirico, Warren, NJ (US); Ernest Balestracci, Iselin, NJ (US); Daniel Darst, Zimmerman, MN (US); Eric J. Krause, Big Lake, MN (US); Vishal N. Lokhande, Mountain View, CA (US); Jacob S. Childs, Minneapolis, MN (US); Peter B. Madson, Shanghai (CN); Daniel V. Clements, Minneapolis, MN (US)

(73) Assignee: Bracco Diagnostics Inc., Princeton, NJ (US)

( * ) Notice: Subject to any disclaimer, the term of this patent is extended or adjusted under 35 U.S.C. 154(b) by 1113 days.

(21) Appl. No.: 12/137,356

(22) Filed: Jun. 11, 2008

(65) Prior Publication Data

US 2009/0318745 A1    Dec. 24, 2009

(51) Int. Cl.
*A61N 5/00* (2006.01)
(52) U.S. Cl. ............................................................. 600/5
(58) Field of Classification Search .................. 128/897, 128/898; 280/47.34, 47.35, 79.11, 79.3; 208/638, 651, 33.992, 79.5, 79.6
See application file for complete search history.

(56) References Cited

U.S. PATENT DOCUMENTS

| 3,483,867 A | 12/1969 | Markovitz |
| 3,710,118 A | 1/1973 | Holgate et al. |
| 3,714,429 A | 1/1973 | Mozley |
| 3,774,036 A | 11/1973 | Gerhart |
| 3,997,784 A | 12/1976 | Picunko et al. |
| 4,096,859 A | 6/1978 | Agarwal |
| 4,286,169 A | 8/1981 | Rossem |
| 4,336,036 A | 6/1982 | Leeke |
| 4,466,888 A | 8/1984 | Verkaart |
| 4,562,829 A | 1/1986 | Bergner |
| 4,585,009 A | 4/1986 | Barker et al. |
| 4,585,941 A | 4/1986 | Bergner |

(Continued)

FOREIGN PATENT DOCUMENTS

EP    0102121 A1    3/1984

(Continued)

OTHER PUBLICATIONS

Neil J. Epstein, et al., "A Rb82 infusion system for quantitative perfusion imaging with 3D PET" Applied Radiation and Isotopes, vol. 60, Feb. 9, 2004, pp. 921-927, XP002557544 DOI:10, 1016/j.apradiso.2004.02.002.

(Continued)

*Primary Examiner* — Samuel Gilbert
(74) *Attorney, Agent, or Firm* — Fredrikson & Byron, PA

(57) ABSTRACT

A shielding assembly for an infusion system includes a plurality of compartments and a door for each compartment, and provides a radioactive radiation barrier for the compartments. One of the compartments contains a radioisotope generator of the infusion system and another of the compartments may contain a waste bottle of the infusion system. An opening into each of the generator and waste bottle compartments may be oriented upward, and the opening into the latter may be at a higher elevation than the opening into the former, for example, to facilitate independent removal and replacement of each. A door of at least one of the compartments, other than the generator compartment, when closed, may prevent the door of the generator compartment from being opened. A cabinet structure for the infusion system may enclose the shielding assembly and secure the generator.

37 Claims, 23 Drawing Sheets

U.S. PATENT DOCUMENTS

| | | | |
|---|---|---|---|
| 4,623,102 A | 11/1986 | Hough, Jr. |
| 4,625,118 A | 11/1986 | Kriwetz et al. |
| 4,679,142 A | 7/1987 | Lee |
| 4,755,679 A | 7/1988 | Wong |
| 4,769,008 A | 9/1988 | Hessel |
| 4,853,546 A | 8/1989 | Abe et al. |
| 4,994,056 A | 2/1991 | Ikeda |
| 5,039,863 A | 8/1991 | Matsuno et al. |
| 5,258,906 A | 11/1993 | Kroll et al. |
| 5,274,239 A | 12/1993 | Lane et al. |
| 5,395,320 A | 3/1995 | Padda |
| 5,475,232 A | 12/1995 | Powers et al. |
| 5,485,831 A | 1/1996 | Holdsworth et al. |
| 5,590,648 A | 1/1997 | Mitchell et al. |
| 5,702,115 A | 12/1997 | Pool |
| 5,739,508 A | 4/1998 | Uber, III |
| 5,765,842 A | 6/1998 | Phaneuf |
| 5,827,429 A | 10/1998 | Ruschke |
| 5,840,026 A | 11/1998 | Uber, III et al. |
| 5,885,216 A | 3/1999 | Evans, III et al. |
| 6,157,036 A | 12/2000 | Whiting et al. |
| 6,347,711 B1 | 2/2002 | Goebel |
| 6,442,418 B1 | 8/2002 | Evans, III et al. |
| 6,558,125 B1 | 5/2003 | Futterknecht |
| 6,626,862 B1 | 9/2003 | Duchon et al. |
| 6,767,319 B2 | 7/2004 | Reilly et al. |
| 6,870,175 B2 | 3/2005 | Dell et al. |
| 6,901,283 B2 | 5/2005 | Evans, III et al. |
| 6,908,598 B2 | 6/2005 | Sylvester |
| 7,163,031 B2 | 1/2007 | Graves et al. |
| 7,169,135 B2 | 1/2007 | Duchon et al. |
| 7,204,797 B2 | 4/2007 | Reilly et al. |
| 7,256,888 B2 | 8/2007 | Staehr et al. |
| 7,413,123 B2 | 8/2008 | Ortenzi |
| 7,476,377 B2 | 1/2009 | Moller |
| 7,504,646 B2 | 3/2009 | Balestracci |
| 7,612,999 B2 | 11/2009 | Clark |
| 7,862,534 B2 | 1/2011 | Quirico |
| 2003/0004463 A1 | 1/2003 | Reilly |
| 2003/0139640 A1 | 7/2003 | Whittacre |
| 2004/0104160 A1 | 6/2004 | Scagliarini |
| 2005/0187515 A1 | 8/2005 | Varrichio |
| 2005/0277833 A1 | 12/2005 | Williams |
| 2005/0278066 A1 | 12/2005 | Graves et al. |
| 2006/0015056 A1 | 1/2006 | Ellingboe |
| 2006/0151048 A1 | 7/2006 | Tochon-Danguy |
| 2007/0140958 A1 | 6/2007 | DeKemp |
| 2007/0213848 A1 | 9/2007 | DeKemp et al. |
| 2007/0232980 A1 | 10/2007 | Felt |
| 2007/0282263 A1 | 12/2007 | Kalafut et al. |
| 2008/0071219 A1 | 3/2008 | Rhinehart et al. |
| 2008/0093564 A1 | 4/2008 | Tartaglia et al. |
| 2008/0166292 A1 | 7/2008 | Levin et al. |
| 2008/0177126 A1* | 7/2008 | Tate et al. ............ 600/5 |
| 2008/0242915 A1 | 10/2008 | Jackson et al. |
| 2009/0309466 A1 | 12/2009 | Quirico |
| 2009/0312630 A1 | 12/2009 | Hidem |
| 2009/0312635 A1 | 12/2009 | Shimchuk |
| 2010/0125243 A1 | 5/2010 | Balestracci |
| 2010/0270226 A1 | 10/2010 | Balestracci |
| 2010/0312039 A1 | 12/2010 | Quirico |
| 2011/0071392 A1 | 3/2011 | Quirico |
| 2011/0172524 A1 | 7/2011 | Hidem |

FOREIGN PATENT DOCUMENTS

| | | |
|---|---|---|
| EP | 0160303 | 11/1985 |
| EP | 0310148 | 4/1989 |
| EP | 0919249 | 6/1999 |
| EP | 1421960 | 5/2004 |
| FR | 2867084 | 9/2005 |
| JP | 2000350783 | 12/2000 |
| JP | 2006325826 | 12/2006 |
| WO | 9615337 | 5/1996 |
| WO | 9956117 | 11/1999 |
| WO | 02096335 | 12/2002 |
| WO | 2004059661 | 7/2004 |
| WO | 2005002971 | 1/2005 |
| WO | 2006007750 A1 | 1/2006 |
| WO | 2006026603 | 3/2006 |
| WO | 2006074473 | 7/2006 |
| WO | 2006129301 | 12/2006 |
| WO | 2006135374 | 12/2006 |
| WO | 2007016170 A1 | 2/2007 |
| WO | 2007030249 A2 | 3/2007 |
| WO | 2007071022 A1 | 6/2007 |
| WO | 2007104133 A1 | 9/2007 |
| WO | 2007149108 A2 | 12/2007 |
| WO | 2008028165 | 3/2008 |
| WO | 2008037939 | 4/2008 |
| WO | 2008082966 | 7/2008 |
| WO | 2008140351 | 11/2008 |
| WO | 2008140351 A1 | 11/2008 |
| WO | 2009152320 | 12/2009 |
| WO | 2010020596 | 2/2010 |

OTHER PUBLICATIONS

R. Klein, et al., "Precision controlled elution of a Sr82/Rb82 generator for cardiac perfusion imaging with positron emission tomography" Physics in Medicine and Biology, vol. 52, Jan. 11, 2007, pp. 659-673, XP002557545 DOI:10, 1088/0031-9155/52/3/009.

International Search Report and Written Opinion, dated Feb. 25, 2010 for PCT Application No. PCT/US2009/047027, 22 pages.

International Search Report and Written Opinion, dated Feb. 17, 2010 for PCT Application No. PCT/US2009/047030, 17 pages.

International Search Report and Written Opinion, dated Mar. 1, 2010 for PCT Application No. PCT/US2009/047031, 20 pages.

International Search Report and Written Opinion, dated Feb. 25, 2010 for PCT Application No. PCT/US2009/047034, 15 pages.

Brochure, "IV and Liquid Filters: Speedflow Adult 0.2 um Positive", http://www.gvs.it/flex/FixedPages/UK/LiquidFilters.php/L/UK/ID/Speedflow%20Adjust% . . . taken off of web on Nov. 11, 2008.

International Search Report and Written Opinion, dated Jan. 4, 2010 for PCT Application No. PCT/US2009/063788, 13 pages.

Bracco Brochure, "Rubidium 82 Infusion System, Easy to Operate . . . Automated . . . Complete", (C)Bracco Diagnostics, Inc., 0605-002NA, Jun. 2001. (2 pages).

Imaging Technology News, web exclusive: "FDG-PET Injector Thrusts New Life into Molecular Imaging", Apr. 2008, 2 pages.

Bracco, "Cardio-Gen82® Infusion System User's Guide", Jul. 3, 2007, pp. 1-53.

"Posijet Integrated FDG dispensing and infusion system" May 2008.

* cited by examiner

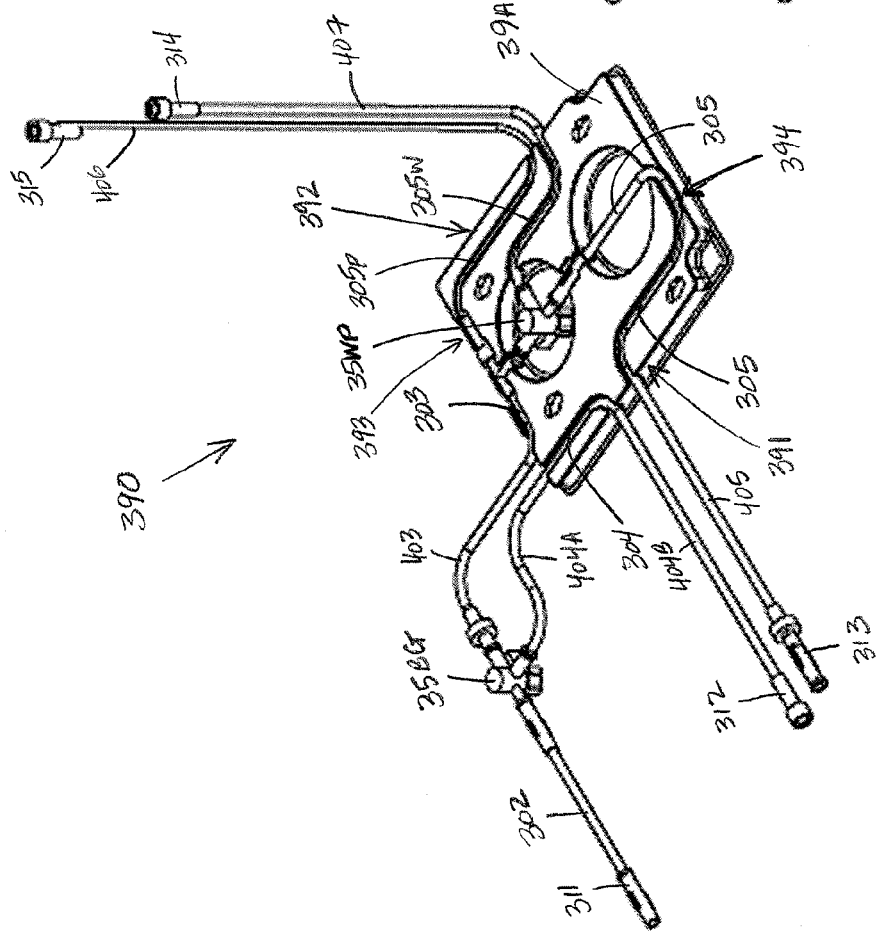
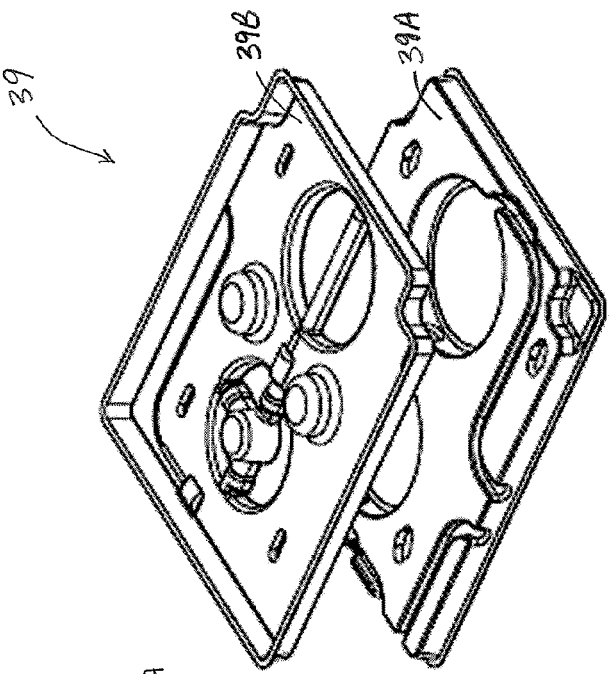
FIGURE 3C
FIGURE 3D

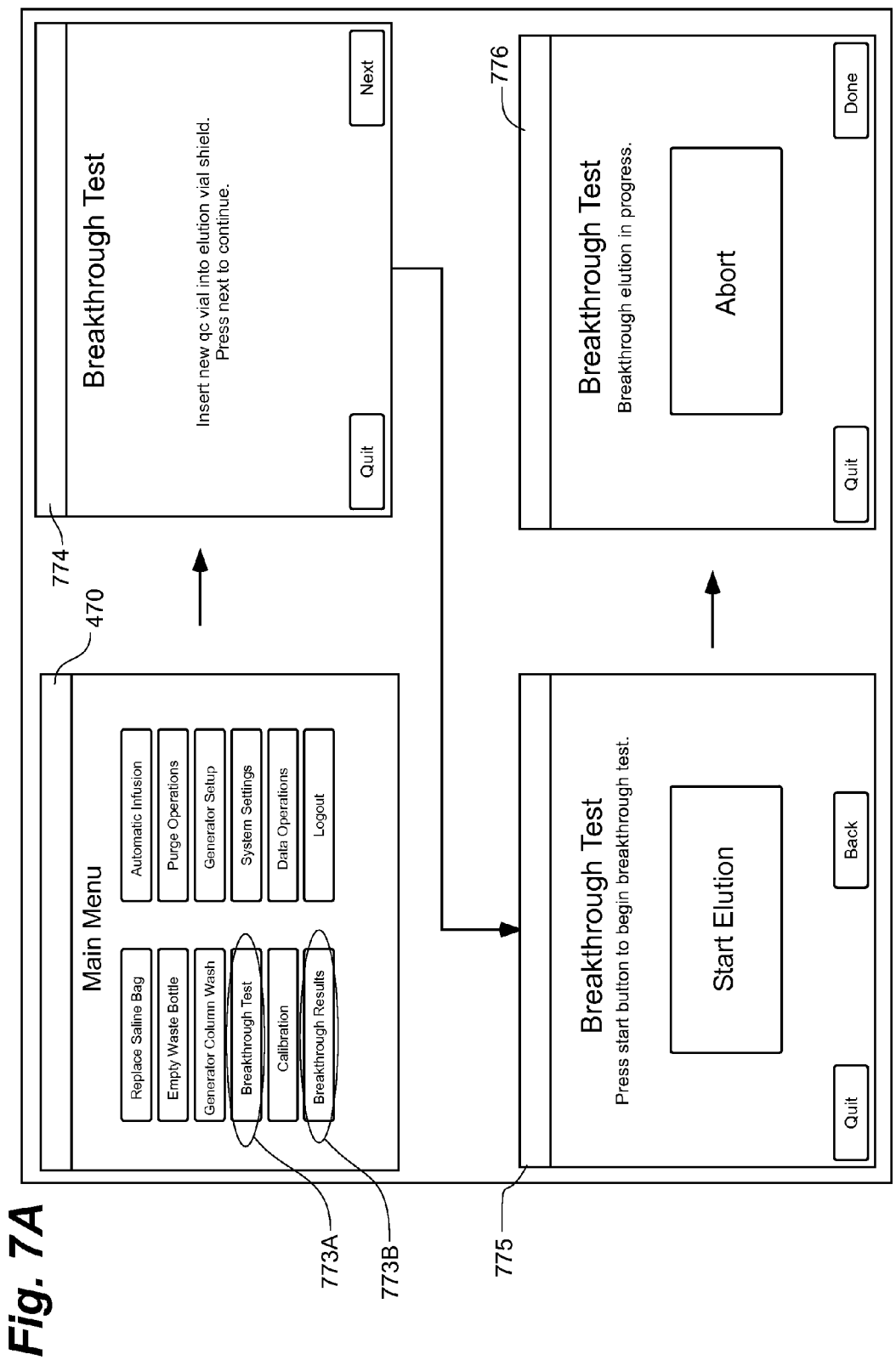

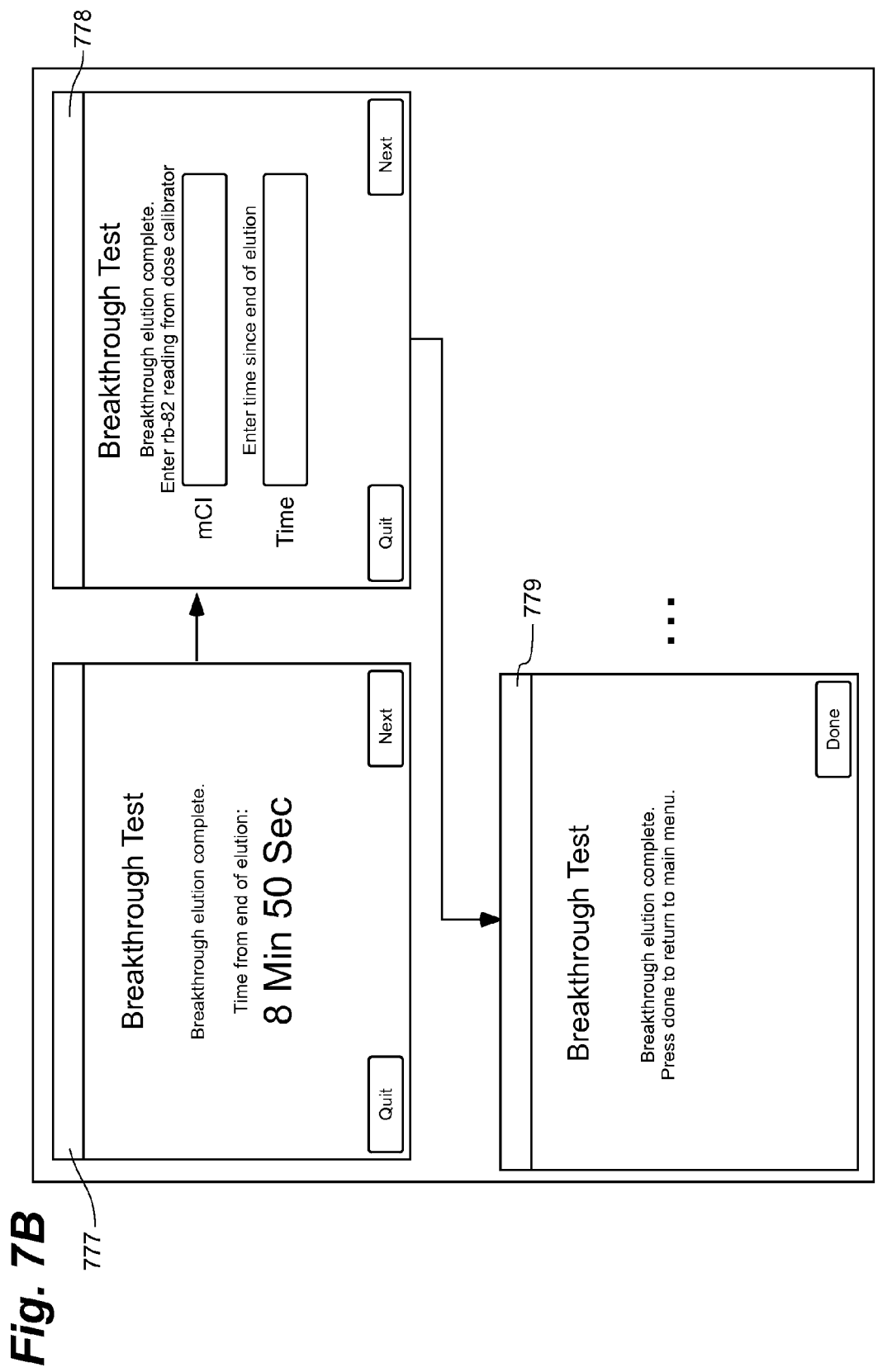

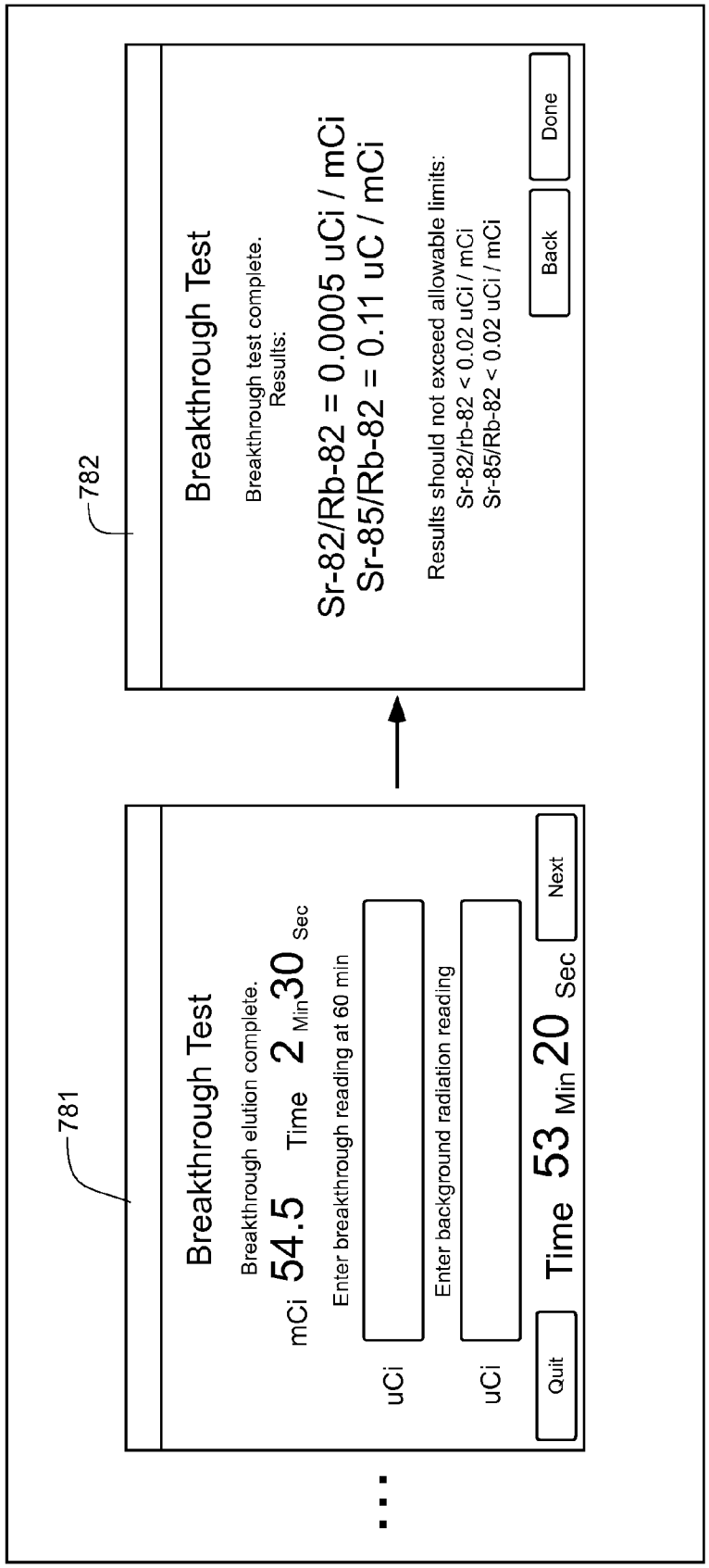

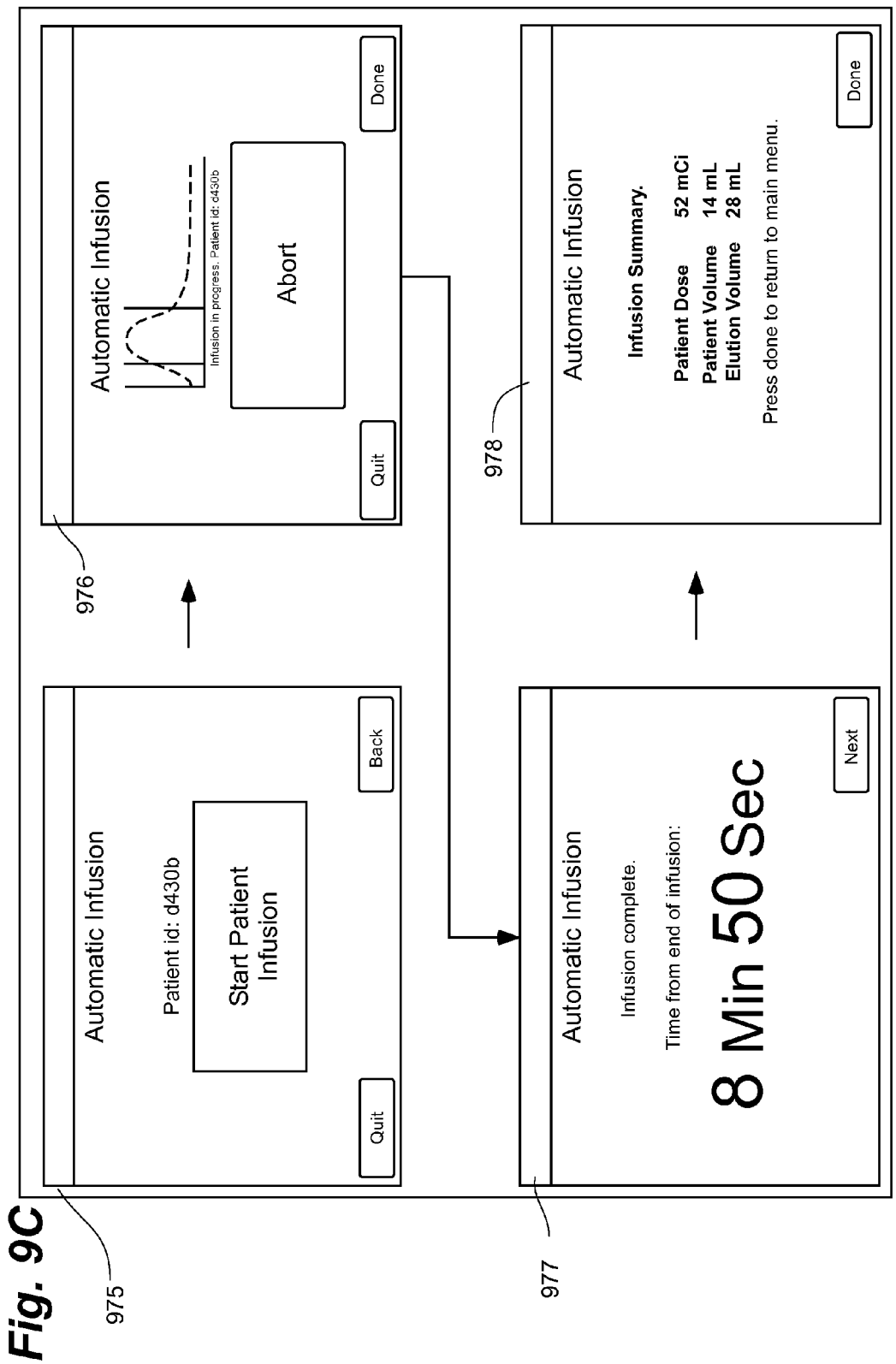

SHIELDING ASSEMBLIES FOR INFUSION SYSTEMS

RELATED APPLICATIONS

The present application is related to the following commonly assigned utility patent applications, all of which are filed concurrently herewith and all of which are hereby incorporated by reference in their entireties: Ser. No. 12/137,363, entitled: INFUSION SYSTEM CONFIGURATIONS; Ser. No. 12/137,364, entitled: INFUSION SYSTEMS INCLUDING COMPUTER-FACILITATED MAINTENANCE AND/OR OPERATION; and Ser. No. 12/137,377, entitled: CABINET STRUCTURES SUPPORTING INFUSION SYSTEMS.

TECHNICAL FIELD

The present invention pertains to systems that generate and infuse radiopharmaceuticals, and, more particularly, to shielding assemblies thereof.

BACKGROUND

Nuclear medicine employs radioactive material for therapy and diagnostic imaging. Positron emission tomography (PET) is one type of diagnostic imaging, which utilizes doses of radiopharmaceutical, for example, generated by elution within a radioisotope generator that are injected, or infused into a patient. The infused dose of radiopharmaceutical is absorbed by cells of a target organ, of the patient, and emits radiation, which is detected by a PET scanner, in order to generate an image of the organ. An example of a radioactive isotope, which may be used for PET, is Rubidium-82 (produced by the decay of Strontium-82); and an example of a radioisotope generator, which yields a saline solution of Rubidium-82, via elution, is the CardioGen-82® available from Bracco Diagnostics Inc. (Princeton, N.J.).

Whether the half-life of a particular radioactive isotope, employed by a radiopharmaceutical, is relatively short or long, a patient undergoing a nuclear imaging procedure is not typically exposed to a significant amount of radiation. However those personnel, whose job it is to set up and maintain radiopharmaceutical infusion systems, and to administer doses therefrom, are subject to more frequent exposures to radiation. Therefore, shielding assemblies, which provide a radiation barrier to protect these personnel from excessive exposure to radiation sources, are an important component of radiopharmaceutical generators and infusion systems. These shielding assemblies are typically formed with lead sidewalls, the bulk and weight of which can pose difficulties for the personnel who regularly set up, maintain and use the systems. Thus, there is a need for improved shielding assemblies employed by systems that generate and infuse radiopharmaceuticals.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

FIG. 3C is a perspective view of a disposable infusion circuit subassembly, according to some embodiments.

FIG. 3D is a frame for the subassembly shown in FIG. 3C, according to some embodiments.

FIGS. 7A-C are schematics showing a fourth group of successive screen shots from the computer interface, according to some embodiments.

FIGS. 9A-C are schematics showing a sixth group of successive screen shots from the computer interface, according to some embodiments.

DETAILED DESCRIPTION

The following detailed description is exemplary in nature and is not intended to limit the scope, applicability, or configuration of the invention in any way. Rather, the following description provides practical illustrations for implementing exemplary embodiments. Utilizing the teaching provided herein, those skilled in the art will recognize that many of the examples have suitable alternatives that can be utilized.

Figure 1A:
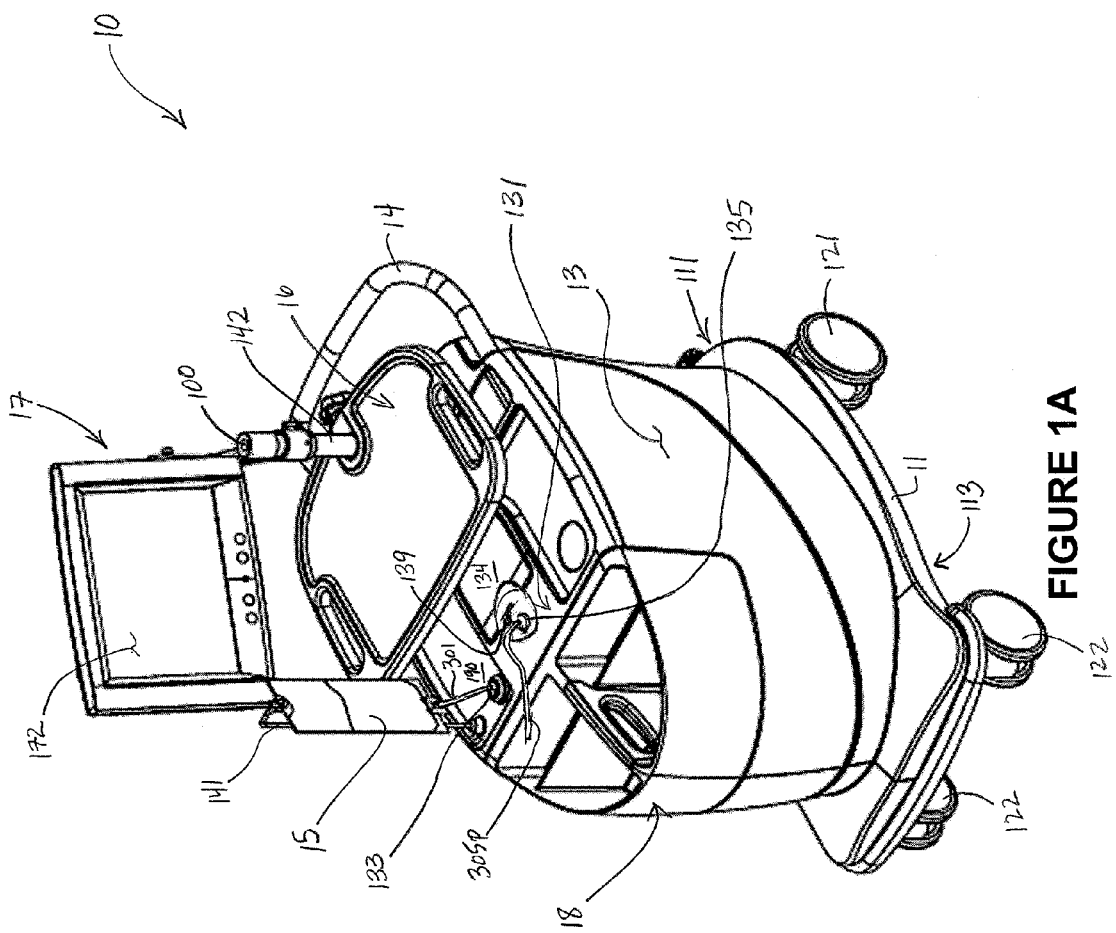
FIG. 1A is a first perspective view of an infusion system, according to some embodiments of the present invention.
Figure 1B:
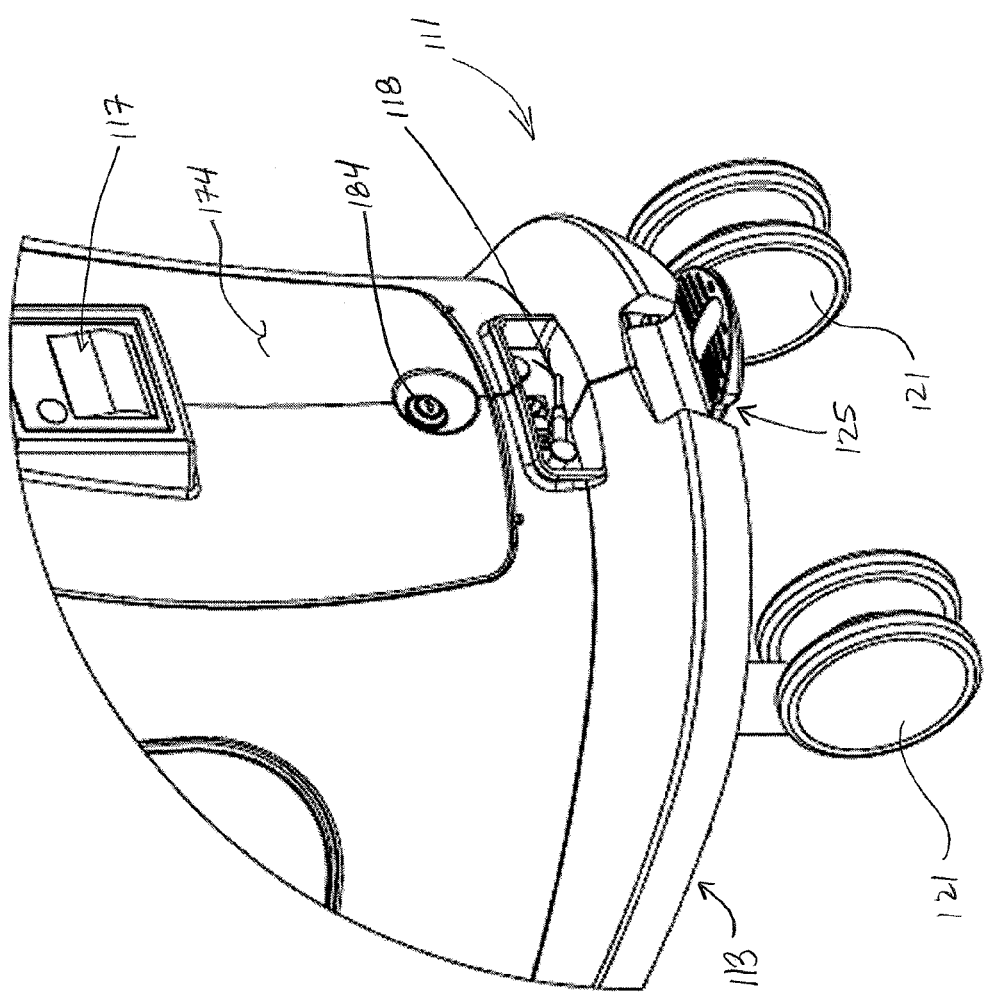
FIG. 1B is another perspective view of a portion of a cabinet structure of the system shown in FIG. 1A, according to some embodiments.
Figure 1C:
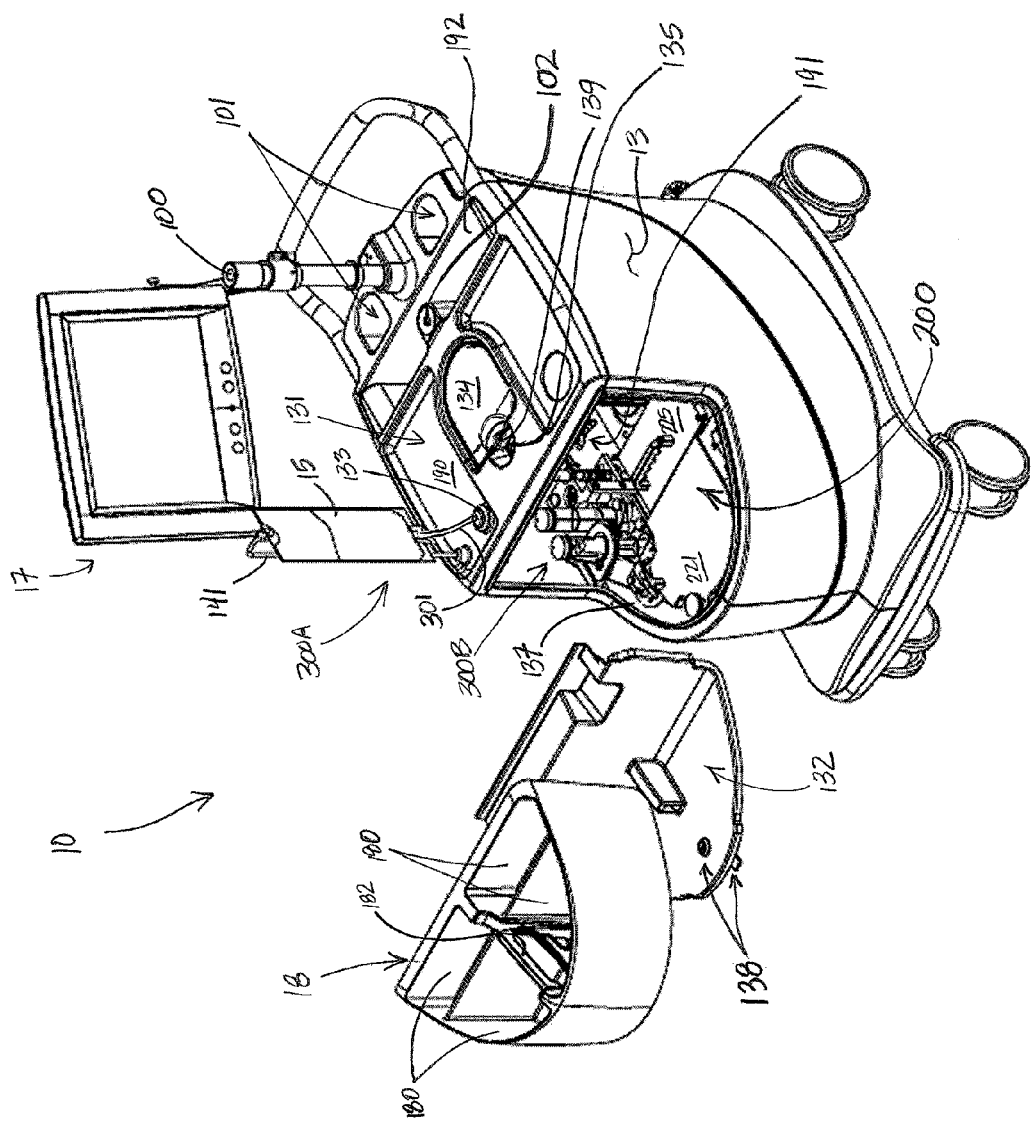
FIG. 1C is a second perspective view of the system shown in FIG. 1A, according to some embodiments.

FIG. 1A is a first perspective view of an infusion system 10, according to some embodiments of the present invention, wherein system 10 is shown supported by a cabinet structure, which includes a platform 113 (seen better in FIG. 2B) and a shell 13; shell 13 extends upward from a skirt 11, that surrounds platform 113, to surrounds an interior space in which a portion of infusion system 10 is contained (—seen in FIG. 1C). Shell may be formed from panels of injection-molded polyurethane fitted together according to methods known to those skilled in the art. FIG. 1A illustrates the cabinet structure of system 10 including a grip or handle 14, which extends laterally from shell 13, in proximity to an upper surface 131 thereof, and a post 142, which extends upward from shell 13, and to which a work surface, or tray 16 and a computer 17 are, preferably, attached, via an ergonomic, positionable mount. According to some embodiments, computer 17 is coupled to a controller of system 10, which is mounted within the interior space surrounded by shell 13, and a monitor 172 of computer 17 not only displays indications of system operation for a user of system 10, but also serves as a device for user input (e.g. touch screen input). However, according to alternate embodiments, another type of user input device, known to those skilled in the art, may be employed by computer 17. Other types of user input devices may included, for example, a keyboard, a series of control buttons or levers, a barcode reader (or other reader of encoded information), a scanner, a computer readable medium containing pertinent data, etc. The user input device may be mounted on the cabinet structure of system 10, as shown, or may be tethered thereto; alternatively the user input device may be remote from system 10, for example, located in a separate control room. According to some additional embodiments, another user input device, for example, in addition to a touch screen of computer 17, may be remote from system 10 and used to start and stop infusions. Operation of system 10, which is facilitated by computer 17, will be described below, in conjunction with FIGS. 4-9C.

FIG. 1A further illustrates two pairs of wheels 121, 122, mounted to an underside of platform 113, to make system 10 mobile; handle 14 is shown located at an elevation suitable for a person to grasp in order to maneuver system 10, from one location for another, upon pairs of wheels 121, 122. According to some preferred embodiments, one or both pairs of wheels 121, 122, are casters, allowing for rotation in a horizontal plane (swivel), in order to provide additional flexibility for maneuvering system 10 in relatively tight spaces.

FIG. 1B is a perspective view of a portion of system 10, on a side 111 of the cabinet structure, which is in proximity to wheels 121. FIG. 1B illustrates a lever or pedal 125, which is located for activation by a foot of the person, who grasps handle 14 to maneuver system 10. In a neutral position, pedal 125 allows wheels 121, 122 to rotate, and, if embodied as casters, to swivel freely. Pedal 125 may be depressed to a first position which prevents a swiveling of wheels 122, according to those embodiments in which wheels 122 are casters, and may be further depressed to brake wheels 121, 122 from rolling and swiveling, upon reaching a desired location. FIG. 1B further illustrates a rear access panel 174, for example, providing access to circuit boards of the aforementioned controller contained within the interior space surrounded shell 13, an optional lock 184, to secure panel 174, a power jack 118, for connecting system 10 to a power source, and a printer 117 for providing documentation of each patient infusion carried out by system 10, and of system quality control test results. In some embodiments, system 10 may further include one or more additional connectors, or ports (not shown), which allow system 10 to be coupled to, for communication with, other devices used for nuclear imaging procedures.

FIG. 1A further illustrates upper surface 131 of shell 13 including several openings 133, 135, 139 formed therein. FIG. 1C is a partially exploded perspective view of system 10, wherein a removable access panel 132 is shown as a contoured portion of upper surface 131, which, when exposed, by lifting away a bin 18, that mates therewith, may be removed from another opening 137 formed in upper surface 131. FIG. 1C also provides a better view of another panel 134 which may be lifted away from opening 139. According to the illustrated embodiment, openings 139 and 137 provide a user of system 10 with independent access to separate portions of infusion system 10, which are contained within shell 13, for example, to set up and maintain system 10; and openings 133 and 135 provide passageways for tubing lines to pass through shell 13. FIG. 1C further illustrates an optional switch 102, which in case of an emergency, may be activated to abort function of system 10. With reference to FIGS. 1A and 1C, it may be appreciated that an arrangement of features formed in upper surface 131 of shell 13, in conjunction with bin 18, tray 16 and computer 17, provide a relatively ergonomic and organized work area for technical personnel who operate system 10.

Figure 1D:
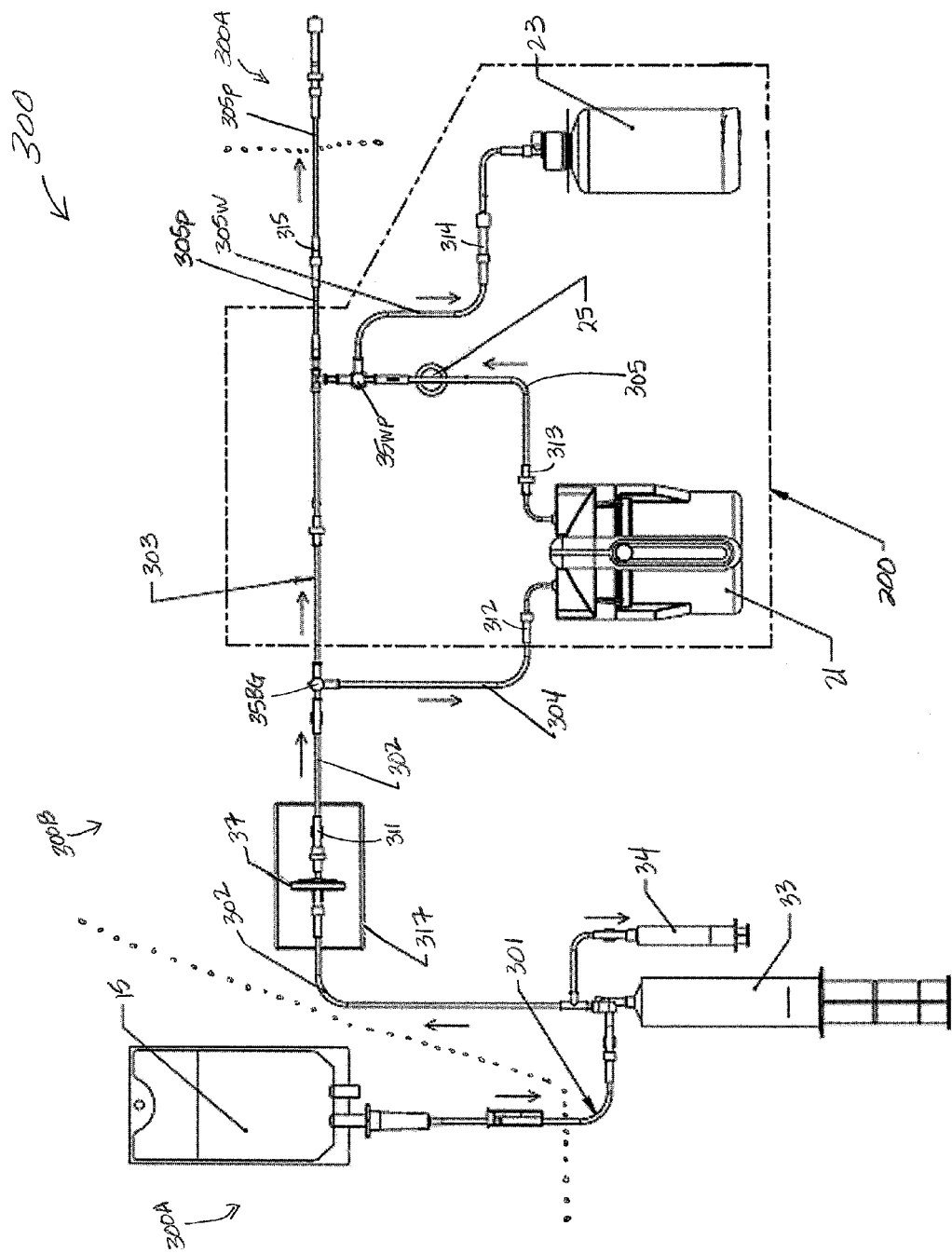
FIG. 1D is a schematic of an infusion circuit, according to some embodiments of the present invention.

Turning now to FIG. 1D, a schematic of an infusion circuit 300, which may be incorporated by system 10, is shown. FIG. 1D illustrates circuit 300 generally divided into a first part 300A, which includes components mounted outside shell 13, and a second part 300B, which includes components mounted within the interior space surrounded by shell 13. (Parts 300A and 300B are delineated by dotted lines in FIG. 1D.) FIG. 1D further illustrates second part 300B of circuit 300 including a portion contained within a shielding assembly 200, which is designated schematically as a dashed line. Some embodiments of shielding assembly 200 will be described in greater detail, in conjunction with FIGS. 2A-B and 3A-B, below.

According to the illustrated embodiment, circuit 300 includes an eluant reservoir 15, for example, a bag, bottle or other container, containing saline as the eluant, which is shown hanging from a post, or hanger 141 above upper surface 131 of shell 13 in FIG. 1A; a syringe pump 33, for pumping the eluant from reservoir 15, and a pressure syringe 34, for monitoring pumping pressure; a filter 37, which may also serve as a bubble trap, for the pumped eluant; a radioisotope generator 21, through which the filtered eluant is pumped to create a radioactive eluate, for example an eluate carrying Rubidium-82 that is generated by the decay of Strontium-82, via elution, within a column of generator 21; and an activity detector 25, for measuring the activity of the eluate discharged from generator 21, in order to provide feedback for directing the flow of the eluate, via a divergence valve 35WP, either to a waste bottle 23 or through a patient line 305p, for example, to inject a dose of the radiopharmaceutical eluate into a patient. With reference back to FIG. 1A, patient line 305p is shown extending out from shell 13, through opening 135, to a distal end thereof, which, according to some embodiments, includes a filter. Patient line 305p may be coupled to another line that includes a patient injection needle (not shown). Alternatively, patient line 305p may be coupled to another line (not shown), which extends from a source of another active substance, for example, a stress agent; the other line is coupled to the line that includes the patient injection needle, in order to permit injection of the additional active substance. FIG. 1D illustrates an eluant tubing line 301 coupled to reservoir 15 and to pump 33, and, with reference to FIGS. 1A-B, it may be appreciated that opening 133 provides the passageway for tubing line 301 to enter the interior space surrounded by shell 13. According to some preferred embodiments, opening 133 includes a grommet-type seal that prevents leakage of eluant, which may spill from reservoir 15, into the interior space through opening 133, while allowing a user to assemble tubing line 301 through opening 133. Likewise opening 135, which provides a passageway for patient line 305p, may include a grommet-type seal.

FIG. 1D further illustrates another eluant tubing line 302 coupled to pump 33 and a divergence valve 35BG, which may either direct pumped eluant through a tubing line 304, to generator 21, or direct the pumped eluant through a by-pass tubing line 303, directly to patient line 305p. Divergence valve 35BG, as well as divergence valve 35WP, which directs eluate from an eluate tubing line 305 either to a waste line 305w or to patient line 305p, may each be automatically operated by a corresponding servomotor (not shown), coupled to the controller (not shown) of system 10, which controller receives feedback from activity detector 25. When system 10 is operating for automatic infusion, to deliver a dose of radiopharmaceutical to a patient, for example, Rubidium-82 for diagnostic imaging, divergence valve 35BG is initially set to direct eluant to generator 21 and divergence valve 35WP is set to direct eluate from generator into waste bottle 23, until activity detector 25 detects the desired activity of the eluate, at which time the feedback from activity detector 25 causes the controller to direct the corresponding servomotor to re-set valve 35WP for diverting the flow of eluate into patient line 305p. According to some embodiments, once a prescribed volume of the eluate has passed through patient line 305p, the controller directs the corresponding servomotor to re-set divergence valve 35BG for diverting the flow of eluant through by-pass line 303 and into patient line 305p in order to flush, or push any eluate remaining in patient line 305p into the patient. According to some embodiments, the controller may also direct the corresponding servomotor to re-set divergence valve 35WP back toward waste bottle 23, prior to the flush through by-pass line 303, in order to prevent back flow of eluant, through line 305, toward generator 21.

With further reference to FIG. 1D, it may be appreciated that shielding assembly 200 encloses those portions of circuit 300 from which radioactive radiation may emanate, with the exception of that portion of patient line 305p, which must extend out from shielding assembly 200 in order to be coupled to the patient for injection, or in order to be coupled to shielded sample vials, as will be described below. Thus, technical personnel, who operate system 10, are protected from radiation by shielding assembly 200, except at those times when an infusion is taking place, or when quality control tests require collection of eluate into sample vials. During infusions and quality control test sample collection, all technical personnel are typically in another room, or otherwise distanced from system 10, in order to avoid exposure to radiation during the infusion, and, according to some preferred embodiments of the present invention, system 10 includes at least one means for informing technical personnel that an infusion is about to take place or is taking place. With reference back to FIGS. 1A and 1C, system 10 is shown including a light projector 100, mounted on post 142. According to the illustrated embodiment, projector 100, projects a light signal upward, for maximum visibility, when pump 33 is pumping eluant and elution is taking place within generator 21, or at all times when pump 33 is pumping eluant. According to some embodiments, the light signal flashes on and off when the eluate is being diverted from generator 21 into waste bottle 23, and the light signal shines steadily when the eluate is being diverted through patient line 305p, or visa versa. According to other embodiments, a projector 100 shines a light having a first color, to indicate that eluate is being diverted to waste bottle 23, and then shines a light having a second, different color, to indicate that eluate is being directed to patient line 305p for infusion. Light projector 100 may further project a more rapidly flashing light, for example, for approximately five seconds, once a peak bolus of radioactivity is detected in the eluate, to provide further information to technical personnel. Alternative means of informing technical personnel that an infusion is taking place may also be incorporated by system 10, for example, including audible alarms or other types of visible or readable signals that are apparent at a distance from system, including in the control room.

When maintenance of system 10 requires the emptying waste bottle 23, relatively easy access to waste bottle 23 is provided through opening 139 in top surface 131 of shell 13. It should be noted that technical personnel are preferably trained to empty waste bottle 23 at times when the eluate, contained in waste bottle 23, has decayed sufficiently to ensure that the radioactivity thereof has fallen below a threshold to be safe. Opening 139 is preferably located at an elevation of between approximately 2 feet and approximately 3 feet; for example, opening 139 may be at an elevation of approximately 24 inches, with respect to a lower surface of platform 113, or at an elevation of approximately 32 inches, with respect to a ground surface upon which wheels 121, 122 rest. According to the illustrated embodiment, opening 139 is accessed by lifting panel 134; just within opening 139, a shielded lid or door 223 (FIG. 2A) may be lifted away from a compartment of shielding assembly 200 that contains waste bottle 23. With further reference to FIG. 1C, it may be appreciated that opening 137 provides access to other portions of circuit 300 for additional maintenance procedures, such as changing out generator 21 and/or other components of circuit 300, as will be described below.

FIGS. 1A and 1C further illustrate a pair of relatively shallow external recesses 190, which are formed in upper surface 131 of shell 13, for example, in order to catch any spills from infusion system; one of recesses 190 is shown located in proximity to post, or hanger 141, which holds reservoir 15, and in proximity to opening 133, through which tubing line 301 passes. Another recess 192 is shown formed in upper surface 131; a width and depth of recess 192 may accommodate storage of technical documentation associated with infusion system 10, for example, a technical manual and/or maintenance records, or printouts from printer 117 (FIG. 1B). With reference to FIG. 1C, upper surface 131 of shell 13 is shown to also include additional recesses 101, which are each sized to hold a shielded test vial, which contains samples from infusion system 10, for example, for breakthrough testing and/or calibration, which will be described in greater detail, below. Additional receptacles 180 are shown formed in bin 18, on either side of a handle 182, which facilitates removal of bin 18 away from shell 13. Technical personnel may, thus, conveniently transport bin 18 to a storage area for a collection of supplies, for example, sharps, gloves, tubing lines, etc. . . . , into one or more receptacles 180 thereof, and/or to a waste container where separate receptacles 180 of bin 18 may be emptied of waste, such as packaging for the aforementioned supplies, for example, deposited therein during infusion procedures.

Figure 2A:
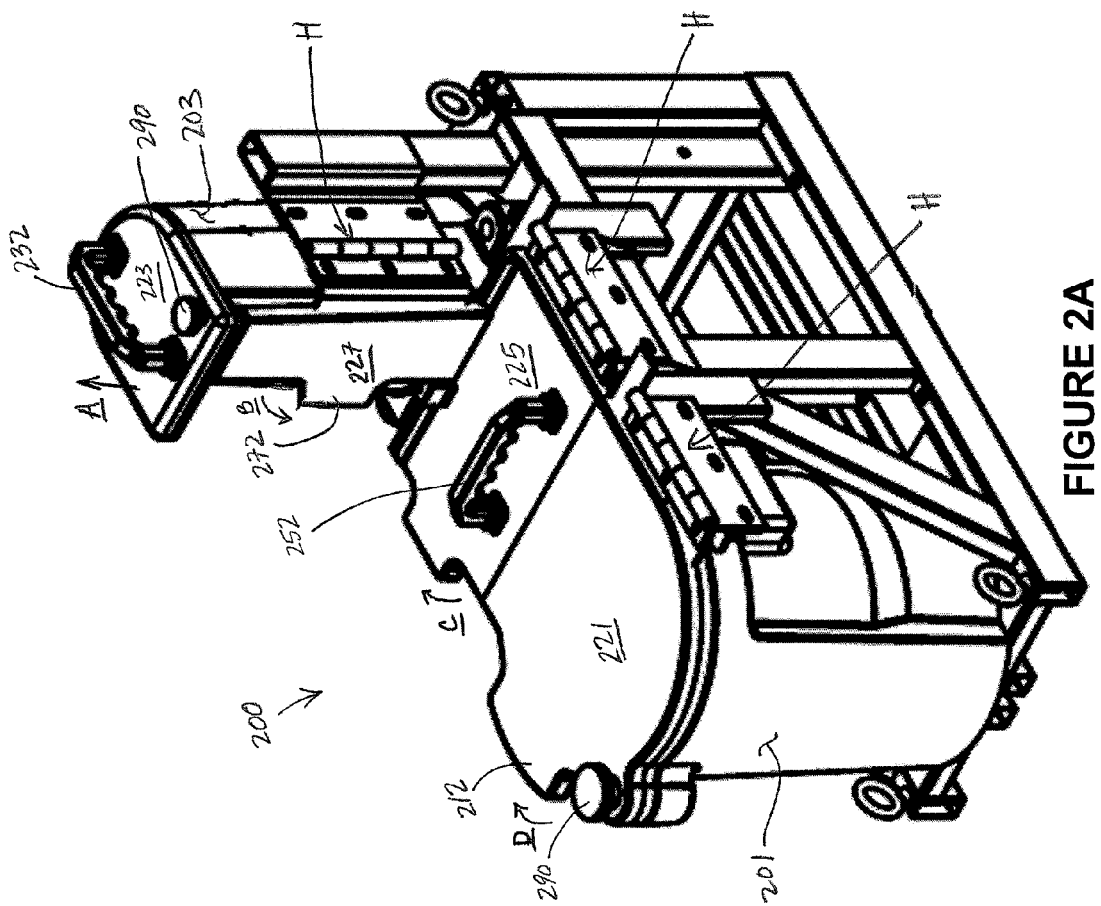
FIG. 2A is a perspective view of a shielding assembly for an infusion system, such as that shown in FIGS. 1A-C, according to some embodiments of the present invention.

FIG. 2A is a perspective view of shielding assembly 200, according to some embodiments of the present invention. With reference to FIGS. 1C and 2A, together, it may be appreciated that opening 137, in upper surface 131 of shell 13, provides access to a lid or door 221 of a sidewall 201 of shielding assembly 200, which sidewall 201 encloses a compartment sized to contain a radioisotope generator of system 10, for example, generator 21, previously introduced. According to the illustrated embodiment, opening 137 and door 221 are located at a lower elevation, for example, with respect to platform 113, than are opening 139 and lid 223, which provide access to the compartment being formed by a sidewall 203 of shielding assembly 200 to contain waste bottle 23, as previously described. When panel 132 is separated from shell 13, and door 221 opened, generator 21 may be lifted out from an opening 231 (FIG. 3A) which mates with door 221 of sidewall 201. A weight of generator 21, which includes its own shielding, may be between approximately 23 and approximately 25 pounds, thus, according to some preferred embodiments of the present invention, the elevation of each of openings 137 and 231, with respect to the lowermost portion of the cabinet structure, is between approximately 1 foot and approximately 2 feet, in order to facilitate an ergonomic stance for technical personnel to lift generator 21 out from the compartment. According to an exemplary embodiment, when shielding assembly 200 is contained in the cabinet structure of FIG. 1A, openings 137 and 231 are located at an elevation of approximately 12 inches, with respect to the lower surface of platform 113, or at an elevation of approximately 19 inches, with respect to the ground surface upon which wheels 121, 122 rest. FIG. 1C further illustrates access panel 132 including a security lock 138, which mates with a framework 19 of system 10, shown in FIG. 2B, in order to limit access to generator 21.

FIGS. 1C and 2A further illustrate a lid or a door 225 of another sidewall 205 (FIG. 3A) of shielding assembly 200, which encloses another compartment that is accessible through opening 137 of shell 13, and which is located adjacent the compartment enclosed by sidewall 201. Each of doors 221, 225 are shown being attached by a corresponding hinge H, and another door 227 is shown attached to sidewall 203 by another hinge H. FIG. 2A illustrates each of lid 223 and doors 221, 225, 227 including a handle 232, 212, 252 and 272, respectively, for moving lid 223 and doors 221, 225, 227, in order to provide access to the corresponding compartments, which can be seen in FIGS. 3A-B. FIG. 2A further illustrates optional thumb screws 290, one securing lid 223 to sidewall 203 and another securing door 221 to sidewall 201, or other means for securing the doors, which are known to those skilled in the art, may be incorporated. Each sidewall 201, 203, 205 and the corresponding lid/door 223, 221, 225, 227 thereof may be individually cast from 3% antimony lead, or from other known shielding materials, and then assembled together according to methods known to those skilled in the art.

Figure 2B:
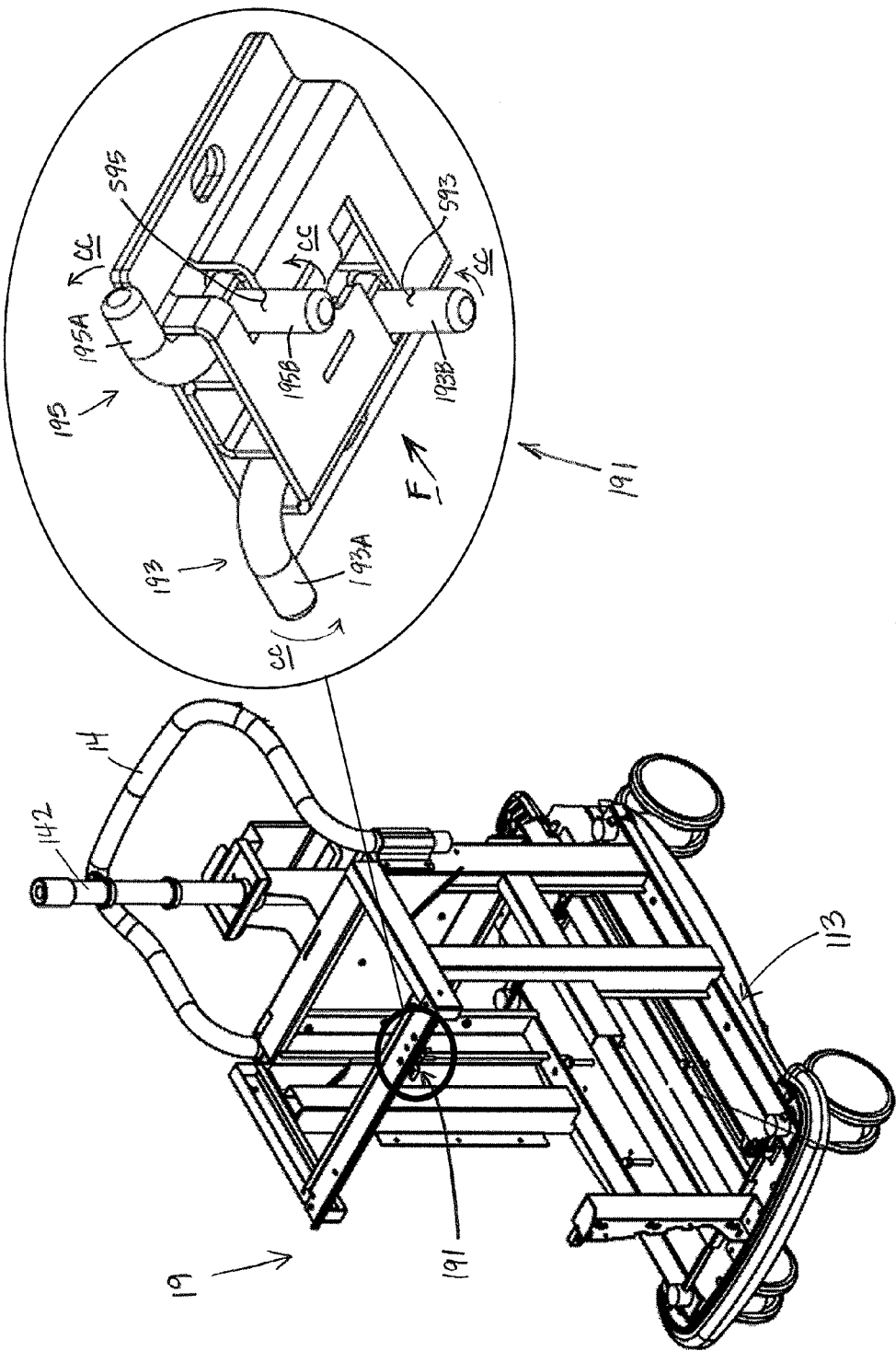
FIG. 2B is a perspective view of a framework of the system, according to some embodiments, with an enlarged detailed view of a component of the system, according to some embodiments.

According to the illustrated embodiment, doors 221, 225 are hinged to open in an upward direction, per arrows D and C, and, with reference back to FIG. 1C, a latch component 191 is provided to hold each of doors 221, 225 in an opened position, thereby, preventing doors 221, 225 from falling closed, which could pinch/crush fingers of technical personnel and/or tubing lines of circuit 300, when in the midst of a maintenance procedure. FIG. 2B is a perspective view of framework 19 of the cabinet structure of system 10, according to some embodiments, to which latch component 191 is mounted; FIG. 2B includes an enlarged detailed view of latch component 191, according to some embodiments. FIG. 2B illustrates latch component 191 including a first pin 193, corresponding to door 225, and a second pin 195, corresponding to door 221; each pin 193, 195 includes a lever end 193A, 193B, respectively, and a holding end 193B, 195B, respectively. An edge of each door 221, 225, upon opening of doors 221, 225, may push past the holding end 195B, 193B of the corresponding pin 195, 193, in a first direction, per arrow F, and then may rest against a respective side S95 and S93 of each end 195B, 193B, until the corresponding lever end 195A, 193A is rotated in a counter-clockwise direction, per arrow cc, thereby moving the corresponding holding end 193B, 195B to make way for the closing of doors 221, 225. Doors 221, 225 being held by latch component 191 in an open position may also be seen in FIG. 3A.

With further reference to FIG. 2A, according to some preferred embodiments of the present invention, an edge of door 225 overlaps door 221 to prevent door 221 from being opened, per arrow D, if door 225 is not opened, per arrow C; and an edge of door 227 overlaps an edge of door 225 to prevent door 225 from being opened if door 227 is not opened, per arrow B; and an edge of lid 223 overlaps door 227 to prevent door 227 from being opened if lid 223 is not opened, per arrow A. Thus, access to the compartment enclosed by sidewall 201 and containing generator 21 is only systematically allowed through a sequential opening of lid 223 and doors 227, 225, 221, since, when generator 21 is replaced it is typically desirable to also replace those portions of circuit 300 which are shielded behind lid 223 and doors 227, 225. The routing of these portions of circuit 300 will be described in conjunction with FIGS. 3A-C.

Figure 3A:
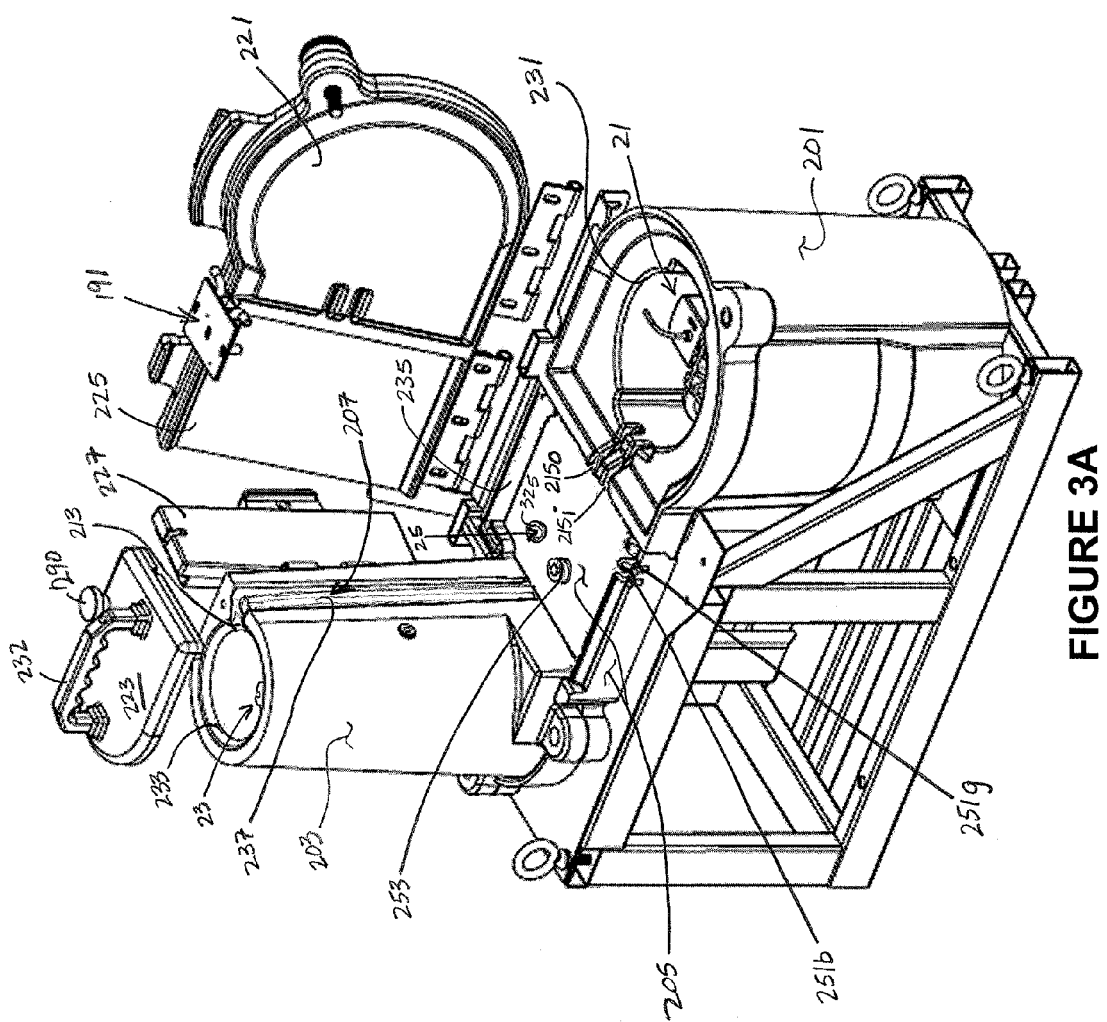
FIG. 3A is another perspective view of the shielding assembly shown in FIG. 2A.

FIG. 3A is another perspective view of shielding assembly 200, according to some embodiments of the present invention. In FIG. 3A, lid 223 and doors 221, 225, and 227 are opened to provide a view into openings 233, 235 and 231 of sidewalls 203, 205 and 201, respectively, and into a passageway 207, which is formed in sidewall 203, opposite the compartment, which contains waste bottle 23. Passageway 207 is shown extending vertically along sidewall 203 and having a grooved extension 213 formed in a perimeter surface of opening 233. An optional retaining member 237, for example, formed from an elongate strip of resilient plastic having a generally c-shape cross-section, is shown being mounted along a length of passageway 207 to hold lines 305$w$ and 305$p$ in place within passageway 207. FIG. 3A further illustrates a pair of passageways 251$b$ and 251$g$, which are formed as grooves in a portion of sidewall 205, and another pair of passageways 215$i$ and 215$o$, which are formed as grooves in a portion of sidewall 201. A routing of portions of tubing circuit 300 (FIG. 1D) through passageways 207, 251$b$, 251$c$, 215$i$ and 215$o$ is shown in FIG. 3B.

Figure 3B:
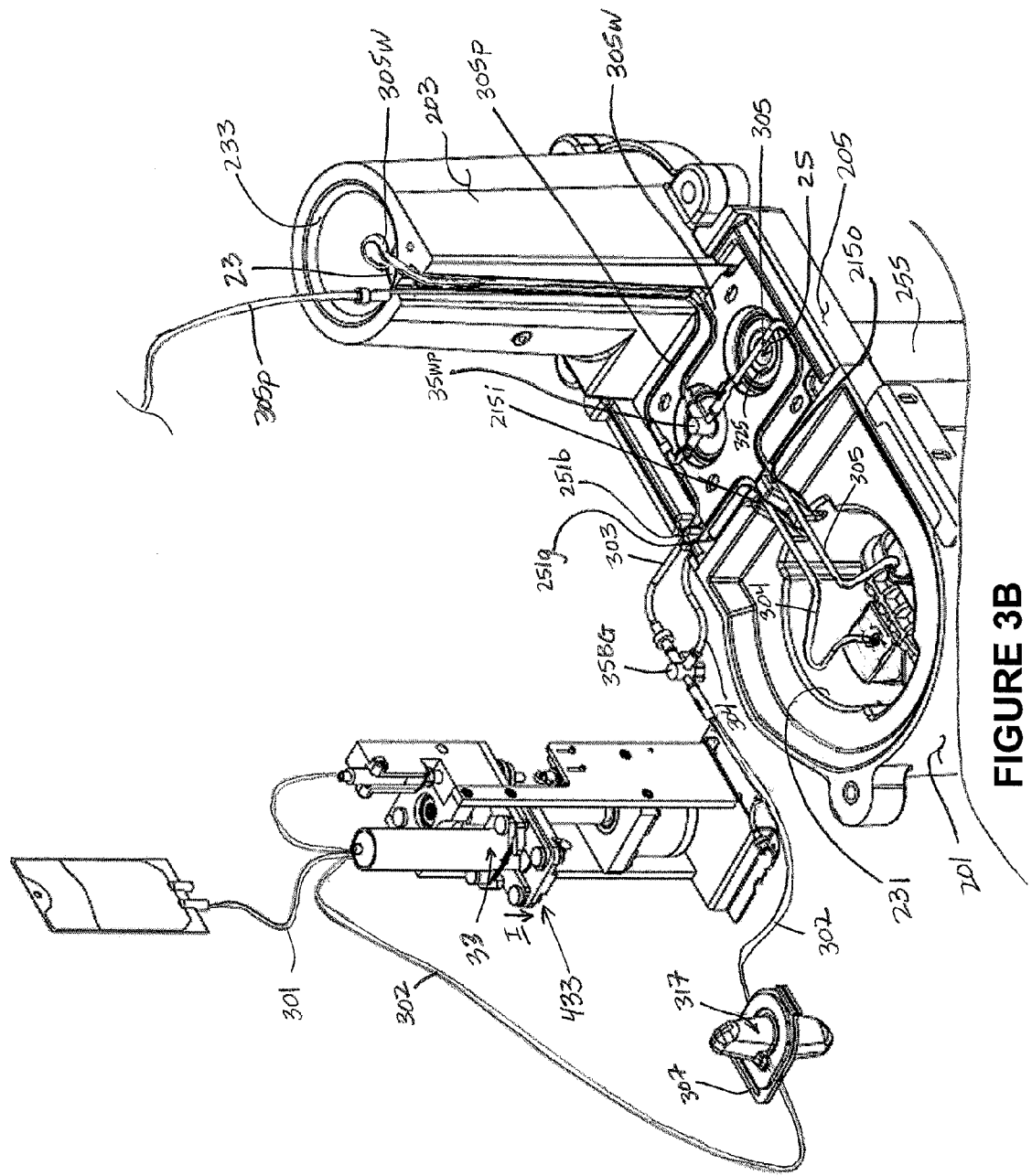
FIG. 3B is a perspective view of the infusion circuit, shown in FIG. 1C, configured and routed, according to some embodiments.

FIG. 3B illustrates tubing line 304 being routed through passageways 251$g$ and 215$i$, eluate tubing line 305 being routed through passageway 215$o$, and both waste line 305$w$ and patient line 305$p$ being routed along passageway 207. Waste line 305$w$ further extends through grooved extension 213 to waste bottle 23, and patient line 305$p$ further extends outward from shielding assembly 200, for example, to extend out through opening 135 in upper surface 131 of shell 13 (FIG. 1A). According to the illustrated embodiment, each passageway formed in shielding assembly 200, by being accessible along a length thereof, can facilitate a relatively easy routing of the corresponding tubing line therethrough, when the corresponding lid/door is open, and a depth of each passageway prevents pinching and/or crushing of the corresponding tubing line routed therethrough, when the corresponding lid/door is closed down thereover.

FIG. 3A further illustrates sidewall 205 including a valve actuator receptacle 253, into which divergence valve 35WP is mounted, to be controlled by one of the servomotors (not shown) of system 10, and an opening 325 for activity detector 25. Activity detector 25 is mounted in a shielded well 255 that extends downward from opening 325 (shown in FIG. 3B), and, with reference to FIG. 3B, tubing line 305 passes over opening 325 so that detector 25 can detect an activity of the eluate, which passes therethrough. According to some embodiments, the positioning, within the compartment enclosed by sidewall 205, of the components of the portion of infusion circuit 300 which are shown routed therein, is facilitated by providing the components mounted in a frame 39 as a disposable subassembly 390, an embodiment of which is illustrated by FIGS. 3C-D.

FIG. 3C is a perspective view of subassembly 390, and FIG. 3D is a perspective view of frame 39. According to the embodiment illustrated by FIG. 3D, frame 39 is formed from mating trays 39A, 39B, for example, formed from a thermoformed plastic, which fit together to capture, therebetween, and hold, in fixed relation to a perimeter edge of frame 39, divergence valve 35WP and portions of eluant tubing line 304, by-pass tubing line 303, eluate tubing line 305, waste line 305w and patient line 305p. FIG. 3C illustrates the perimeter edge divided into a first side 391, a second side 392, opposite first side 391, a third side 393, extending between first and second sides 391, 392, and a fourth side 394, opposite third side 393. Although FIG. 3D shows trays 39A, 39B individually formed for fitting together, according to alternate embodiments, mating trays of frame 39 may be parts of a continuous sheet of plastic folded over on itself.

According to the illustrated embodiment, an end 404A, of eluant line 304, and an end 403, of by-pass line 303 extend from third side 393 of frame 39 to couple with divergence valve 35BG and an upstream section of eluant tubing line 302. FIG. 3C further illustrates an opposite end 404B of eluant line extending from first side 391 of frame 39, alongside a similarly extending end 405 of eluate line 305, and ends 406 and 407 of patient line 305p and waste line 305w, respectively, extending from second side 392 of frame 39. Although ends 406, 407 are shown extending upward from tray 39a, as they would within shielding assembly 200, it should be appreciated that the tubing lines of circuit 300 are preferably flexible and would drop down under their own weight rather than extending upward, as shown, if not supported. Referring back to FIG. 1D, in conjunction with FIG. 3C, it can be seen that fittings are provided for coupling subassembly 390 into circuit 300: a first fitting 311 couples the section of eluant line 302 to filter 37; a second fitting 312 couples eluant line 304 to an inlet port of generator 21; a third fitting 313, which may incorporate a check valve, couples eluate line 305 to an outlet port of generator 21; a fourth fitting 314 couples waste line 305w to waste bottle 23; and a fifth fitting 315 couples patient line 305p to an extension thereof, which extends outside shell 13 (designated by the dotted line). Each of the fittings 311, 312, 313, 314, 315 may be of the Luer type, or any other suitable type that is known to those skilled in the art.

As previously mentioned, when generator 21 is replaced, it is typically desirable to also replace those portions of circuit 300 which are shielded behind lid 223 and doors 227, 225, and, in those instances wherein system 10 is moved to a new site each day, these portions may be replaced daily. Thus, according to the illustrated embodiment, these portions are conveniently held together by frame 39, as subassembly 390, in order to facilitate relatively speedy removal and replacement, while assuring a proper assembly orientation, via registration with features formed in sidewall 205 (FIG. 3A), for example: registration of divergence valve 35WP with valve actuator receptacle 253, registration of tubing line ends 403 and 404A with passageways 251b and 251g, respectively, registration of tubing line ends 404B and 405 with passageways 215i and 215o, respectively, and registration of tubing line ends 406 and 407 with passageway 207.

With further reference to FIG. 3B, other portions of tubing circuit 300 are shown. FIG. 3B illustrates eluant tubing line 301 extending from reservoir 15, outside of shell 13 (FIG. 1A), to syringe pump 33, which is mounted to an actuating platform 433. According to the illustrated embodiment, platform 433 is actuated by another servomotor (not shown) of system 10, which is controlled by the controller and computer 17 of system 10, to cause a plunger of pump 33 to move, per arrow I, so as to draw in eluant, from reservoir 15, through tubing line 301, and then to cause the plunger to move in the opposite direction so as to pump the eluant, through tubing line 302, to either generator 21 or to by-pass line 303. Although the illustrated embodiment includes syringe pump 33, other suitable pumps, known to those skilled in the art, may be substituted for pump 33, in order to draw eluant from reservoir 15 and to pump the eluant throughout circuit 300. Although not shown, it should be appreciated that divergence valve 35BG is fitted into another valve actuating receptacle mounted within shell 13 and coupled to yet another servomotor (not shown) of system 10.

FIG. 3B further illustrates a filter holder 317 that is mounted alongside an interior surface of shell 13 to hold filter 37 (FIG. 1D) of tubing line 302. Filter holder 317, like frame 39 for subassembly 390, may be formed from a thermoformed plastic sheet; holder 317 may have a clam-shell structure to enclose filter 37 in an interior space, yet allow tubing line 302, on either side of filter 37, to extend out from the interior space, in between opposing sides of the clam-shell structure. Holder 317 is shown including an appendage 307 for hanging holder 317 from a structure (not shown) inside shell 13.

Turning now to FIGS. 4-9C details concerning computer-facilitated operation of system 10 will be described, according to some embodiments of the present invention. As previously mentioned, and with reference back to FIG. 1A, computer 17 of system 10 includes monitor 172, which, preferably, not only displays indications of system operation to inform a user of system 10, but is also configured as a touch screen to receive input from the user. It should be understood that computer 17 is coupled to the controller of system 10, which may be mounted within the interior space surrounded by shell 13. Although FIG. 1A shows computer 17 mounted to post 142 of system 10, for direct hardwiring to the controller of system 10, according to some alternate embodiments, computer 17 is coupled to the controller via a flexible lead that allows computer 17 to be positioned somewhat remotely from those portions of system 10, from which radioactive radiation may emanate; or, according to some other embodiments, computer 17 is wirelessly coupled, for example, via two-way telemetry, to the controller of system 10, for even greater flexibility in positioning computer 17 away from radioactive radiation.

According to some preferred embodiments, computer 17 is pre-programmed to guide the user, via monitor 172, through procedures necessary to maintain system 10, to perform quality control tests on system 10, and to operate system 10 for patient infusions, as well as to interact with the user, via the touch-screen capability of monitor 172, according to preferred embodiments, in order to track volumes of eluant and eluate contained within system 10, to track a time from completion of each elution performed by system 10, to calculate one or more system parameters for the quality control tests, and to perform various data operations. It should be understood that screen shots shown in FIGS. 4-9C are exemplary in nature and are presented to provide an outline of some methods of the present invention in which computer 17 facilitates the aforementioned procedures, without limiting the scope of the invention to any particular computer interface format.

Figure 4:
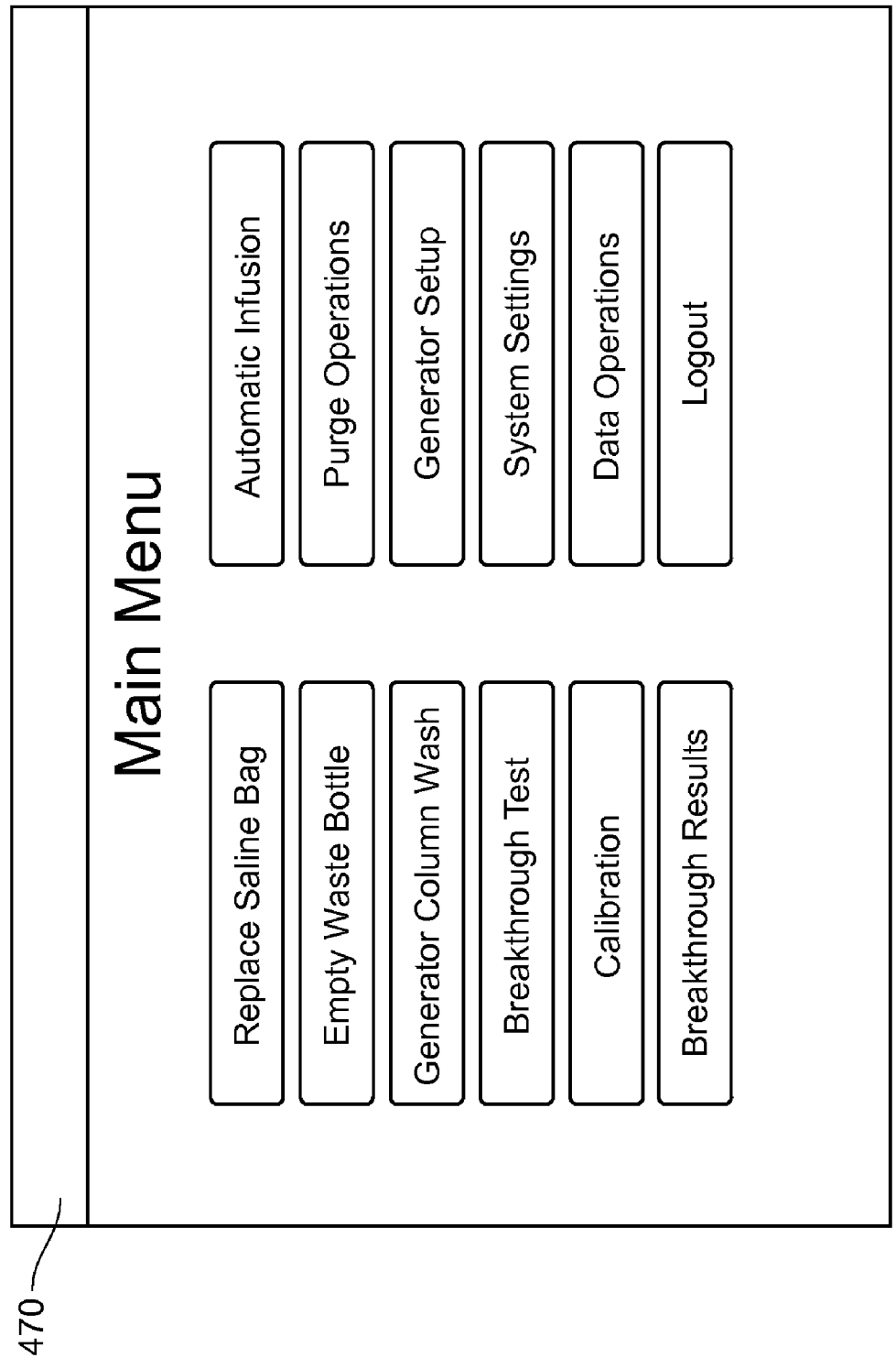
FIG. 4 is a main menu screen shot from an interface of a computer, which may be included in systems of the present invention, according to some embodiments.

FIG. 4 is a screen shot of a main menu 470, which is presented by computer 17 on monitor 172, according to some embodiments. Main menu 470 includes a listing of each computer-facilitated operation that may be selected by the user, once the user has logged on.

Figure 5A:
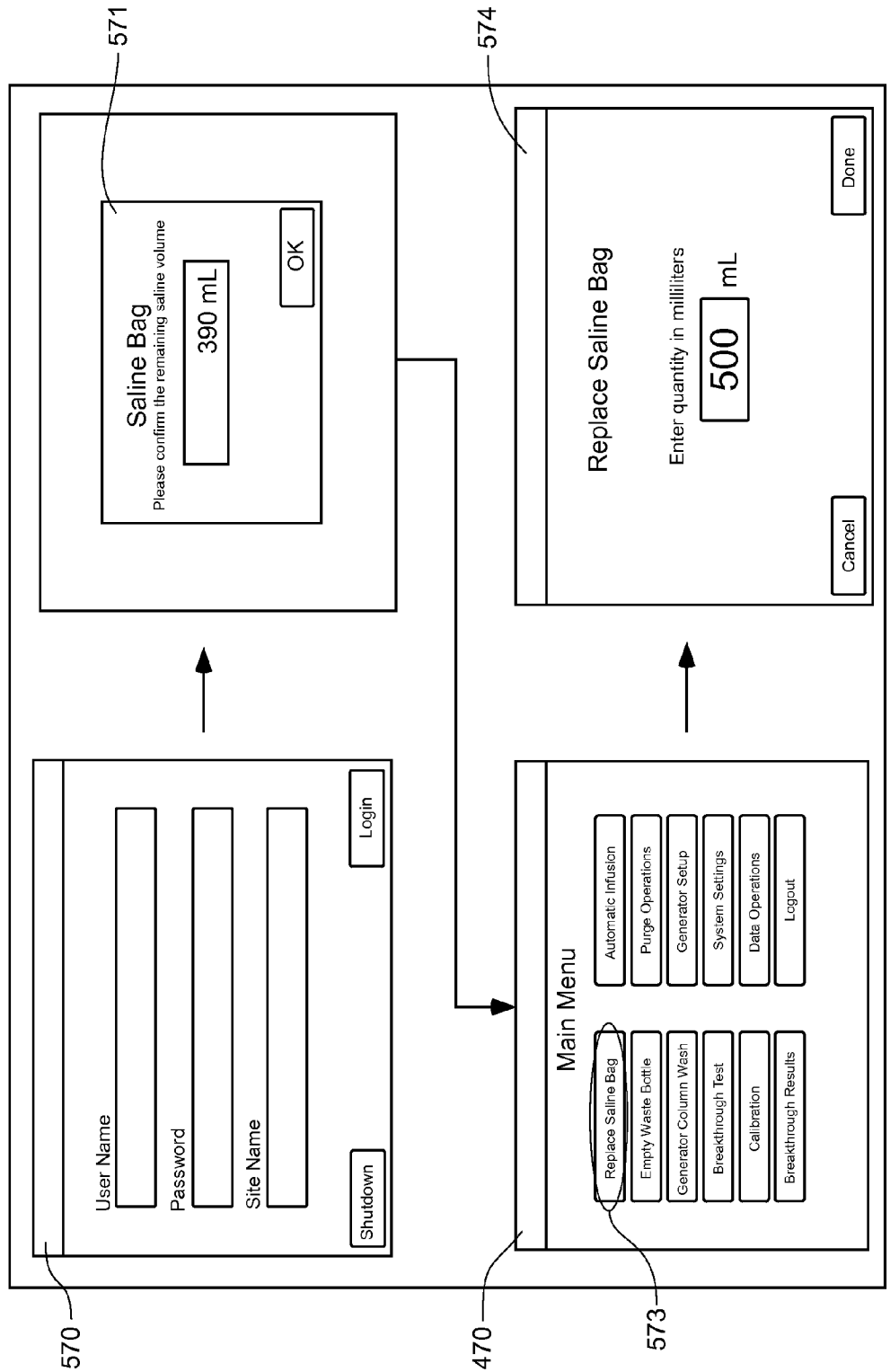
FIG. 5A is a schematic showing a first group of successive screen shots from the computer interface, according to some embodiments.

FIG. 5A is a schematic showing a series of screen shots which includes a log in screen 570. After the user enters the appropriate information into data entry fields of log in screen 570, computer 17 presents a request for the user to confirm the volume of eluant that is within reservoir 15 (e.g. saline in saline bag), via a screen 571, and then brings up main menu 470. According to some embodiments, when the user touch-selects the data entry fields of screen 570 or 571, or of any of the other screens presented herein, below, a virtual keyboard is displayed for touch-select data entry into the selected data entry field; alternately, computer 17 may be augmented with another type of device for user data entry, examples of which include, without limitation, a peripheral keyboard device, a storage medium (i.e. disk) reader, a scanner, a barcode reader (or other reader of encoded information), a hand control (i.e. mouse, joy stick, etc. . . . ).

Figure 5B:
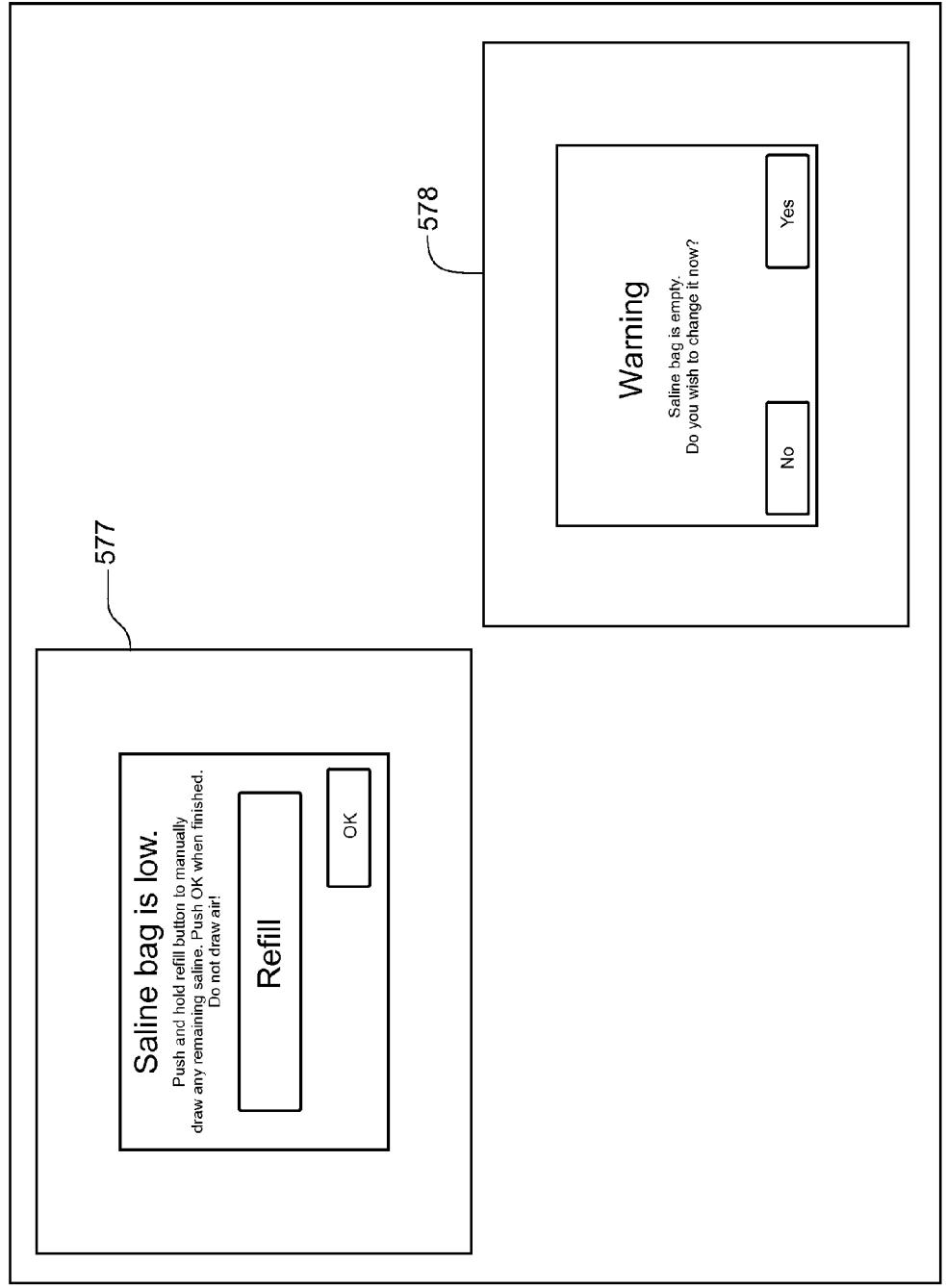
FIG. 5B is a pair of screen shots from the computer interface, which provide indications related to eluant volume levels in a reservoir of the system, according to some embodiments.

If the user determines that the volume of eluant/saline is insufficient, the user selects a menu item 573, to replace the saline bag, which leads computer 17 to prompt the user to enter a quantity of saline contained by the new saline bag, via a screen 574. Thus, computer 17 uses either the confirmed eluant/saline volume, via screen 571, or the newly entered eluant/saline volume, via screen 574, as a baseline from which to track depletion of reservoir volume, via activations of pump 33, in the operation of system 10. With reference to FIG. 5B, during the operation of system 10, when computer 17 detects that the eluant reservoir/saline bag has been depleted to a predetermined volume threshold, computer 17 warns the user, via a screen 577. If the user has disregarded screen 577 and continues to deplete the saline bag, computer 17 detects when the saline bag is empty and provides indication of the same to the user, via a screen 578. To replenish the reservoir/saline bag, the user may either refill the reservoir/bag or replace the empty reservoir/bag with a full reservoir/bag. According to some embodiments, system 10 automatically precludes any further operation of the system until the reservoir is replenished.

Figure 5C:
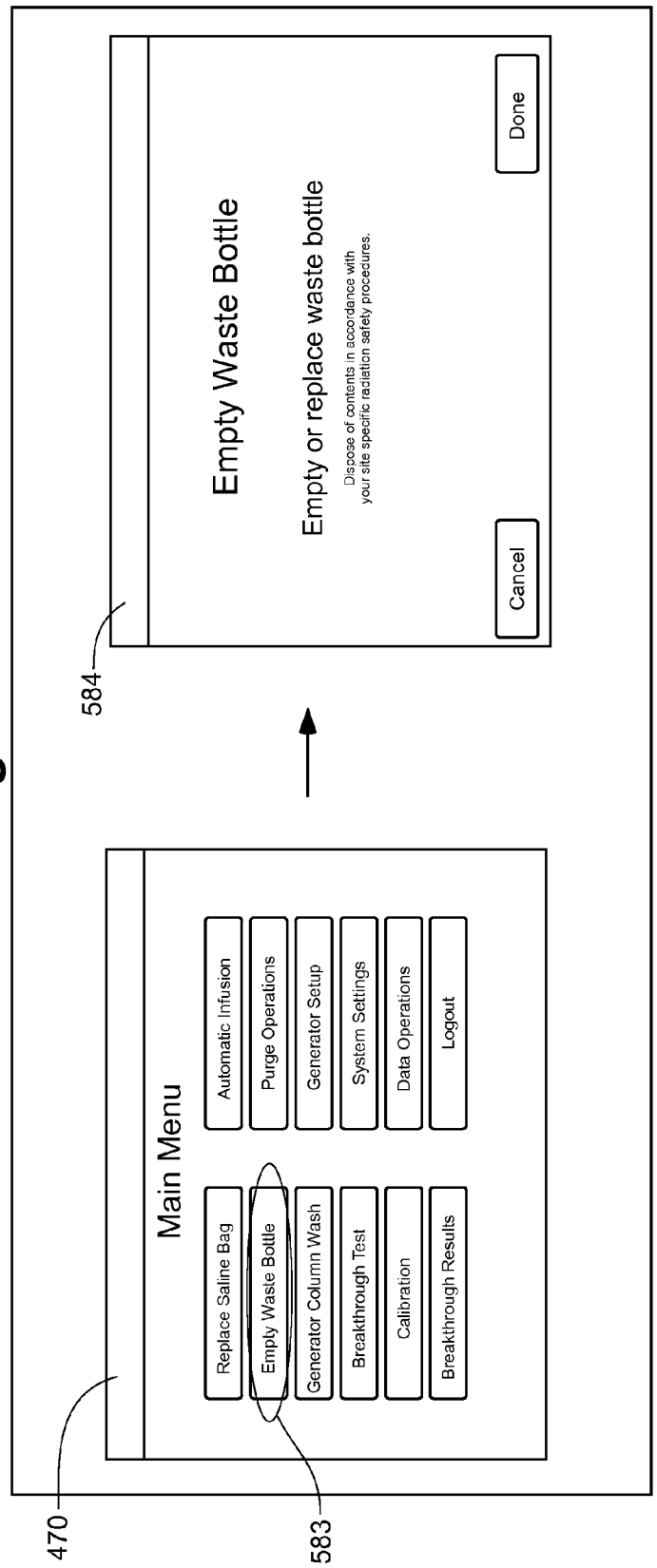
FIG. 5C is a schematic showing a second group of successive screen shots from the computer interface, according to some embodiments.

In addition to tracking the volume of eluant in reservoir 15, computer 17 also tracks a volume of the eluate which is discharged from generator 21 into waste bottle 23. With reference to FIG. 5C, an item 583 is provided in main menu 470, to be selected by the user when the user empties waste bottle 23. When the user selects item 583, computer 17 presents a screen 584, by which the user may effectively command computer 17 to set a waste bottle level indicator to zero, once the user has emptied waste bottle 23. Typically, the user, when powering up system 10 for operation, each day, will either empty waste bottle 23, or confirm that waste bottle 23 was emptied at the end of operation the previous day, and utilize screen 584 to set the waste bottle level indicator to zero. Thus, computer 17, can track the filling of waste bottle 23 via monitoring of the operation of pump 33 and divergence valve 35WP, and provide an indication to the user when waste bottle 23 needs to be emptied, for example, via presentation of screen 584, in order to warn the user that, unless emptied, the waste bottle will overflow. According to some embodiments, system 10 automatically precludes any further operation of the system until the waste bottle is emptied.

Figure 6:
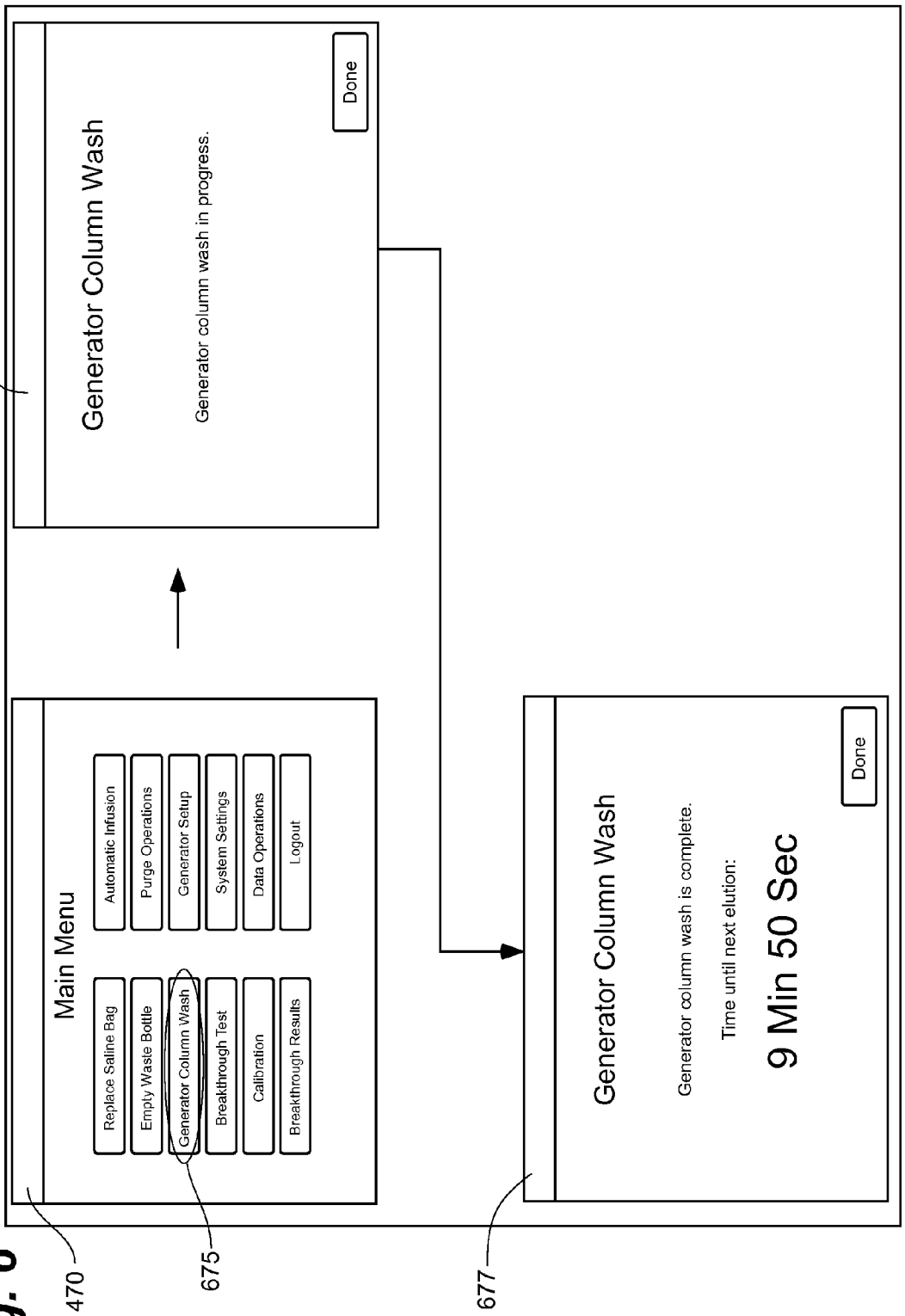
FIG. 6 is a schematic showing a third group of successive screen shots from the computer interface, according to some embodiments.

In addition to the above maintenance steps related to eluant and eluate volumes of system 10, the user of system 10 will typically perform quality control tests each day, prior to any patient infusions. With reference to FIG. 6, according to preferred methods, prior to performing the quality control tests (outlined in conjunction with FIGS. 7A-C and 8A-B), the user may select an item 675 from main menu 470, in order to direct system 10 to wash the column of generator 21. During the generator column wash, which is performed by pumping a predetermined volume of eluant, for example, approximately 50 milliliters, through generator 21 and into waste bottle 23, computer 17 provides an indication, via a screen 676, that the wash is in progress. Also, during the generator column wash, the system may provide a signal to indicate that eluate it being diverted to waste bottle 23, for example, light projector 100 (FIG. 1C) may project a flashing light signal, as previously described.

FIG. 6 further illustrates a screen 677, which is presented by computer 17 upon completion of the column wash, and which provides an indication of a time lapse since the completion of the wash, in terms of a time countdown, until a subsequent elution process may be effectively carried out. While screen 677 is displayed, system 10 may be refilling, from reservoir 15, pump 33, which has a capacity of approximately 55 milliliters, according to some embodiments. According to some preferred embodiments of the present invention, computer 17 starts a timer once any elution process is completed and informs the user of the time lapse, either in terms of the time countdown (screen 677), or in terms of a time from completion of the elution, for example, as will be described in conjunction with FIG. 7B. According to an exemplary embodiment, wherein generator 21 is the CardioGen-82® that yields a saline solution of Rubidium-82, produced by the decay of Strontium-82, via the elution, a time required between two effective elution processes is approximately 10 minutes.

Once the appropriate amount of time has lapsed, after the elution process of generator column wash, a first quality control test may be performed. With reference to FIG. 7A, the user may select, from main menu 470, an item 773A, which directs computer 17 to begin a sequence for breakthrough testing. In conjunction with the selection of item 773A, the user attaches a needle to an end of patient line 305$p$ and inserts the needle into to a test vial, for the collection of an eluate sample therefrom, and, according to FIG. 7A, computer 17 presents a screen 774, which instructs the user to insert the test vial into a vial shield, which may be held in recess 101 of shell 13 (FIG. 1C).

FIG. 7A further illustrates a subsequent screen 775, by which computer 17 receives input, from the user, for system 10 to start the breakthrough elution, followed by a screen 776, which provides both an indication that the elution is in progress and an option for the user to abort the elution. As previously described, the system may provide a signal to indicate that elution is in progress, for example, light projector 100 (FIG. 1C) may project a flashing light signal during that portion of the elution process when eluate is diverted from generator 21 through waste line 305$w$ and into waste bottle 23, and then a steady light signal during that portion of the elution process when the eluate is diverted from generator 21 through patient line 305$p$ and into the test vial, for example, once activity detector 25 detects a dose rate of approximately 1.0 mCi/sec in the eluate discharged from generator 21. Another type of light signal, for example, the more rapidly flashing light, as previously described, may be projected when a peak bolus of radioactivity is detected in the eluate.

Upon completion of the elution process for breakthrough testing, computer 17 presents a screen 777, shown in FIG. 7B, which, like screen 677, provides an indication of a time lapse since the completion of the elution, but now in terms of a time since completion of the breakthrough elution process. When the user transfers the vial containing the sample of eluate into a dose calibrator, to measure the activity of the sample, the user may make a note of the time lapse indicated on screen 777. With further reference to FIG. 7B, once the user has received the activity measure from the dose calibrator, the user proceeds to a screen 778, which includes data entry fields for the activity measure and the time between that at which the dose calibrator measured the activity of the sample and that at which the elution was completed. The user may enter the data via the touch-screen interface of monitor 172, or via any of the other aforementioned devices for user data entry. According to some alternate embodiments, computer 17 may receive the data, electronically, from the dose calibrator, either via wireless communication or a cable connection.

After the data is entered by the user, computer 17 presents screen 779, from which the user moves back to main menu 470 to perform a system calibration, for example, as will be described in conjunction with FIGS. 8A-B, although the breakthrough testing is not completed. With reference back to FIG. 7A, an item 773B is shown, somewhat faded, in main menu 470; item 773B may only be effectively selected following the completion of steps for item 773A, so as to perform a second stage of breakthrough testing. In the second stage, the breakthrough of the sample of eluate collected in the test vial for the breakthrough testing is measured, at a time of approximately 60 minutes from the completion of the elution that produced the sample. With reference to FIG. 7C, after the user has selected item 773B from main menu 470, in order to direct computer 17 to provide breakthrough test results, a screen 781 is displayed. Screen 781 includes, for reference, the values previously entered by the user in screen 778, along with another pair of data entry fields into which the user is instructed to enter the breakthrough reading of the sample at 60 minutes and the background radiation reading, respectively. After the user enters this remaining information, as described above, computer 17 may calculate and then display, on a screen 782, the breakthrough test results. According to the illustrated embodiment, computer 17 also displays on screen 782 pre-programmed allowable limits for the results, so that the user may verify that the breakthrough test results are in compliance with acceptable limits, before moving on to a patient infusion. According to some embodiments, system 10 will not allow an infusion if the results exceed the acceptable limits, and may present a screen explaining that the results are outside the acceptable limits; the screen may further direct the user to contact the generator supplier, for example, to order a replacement generator.

Figure 8A:
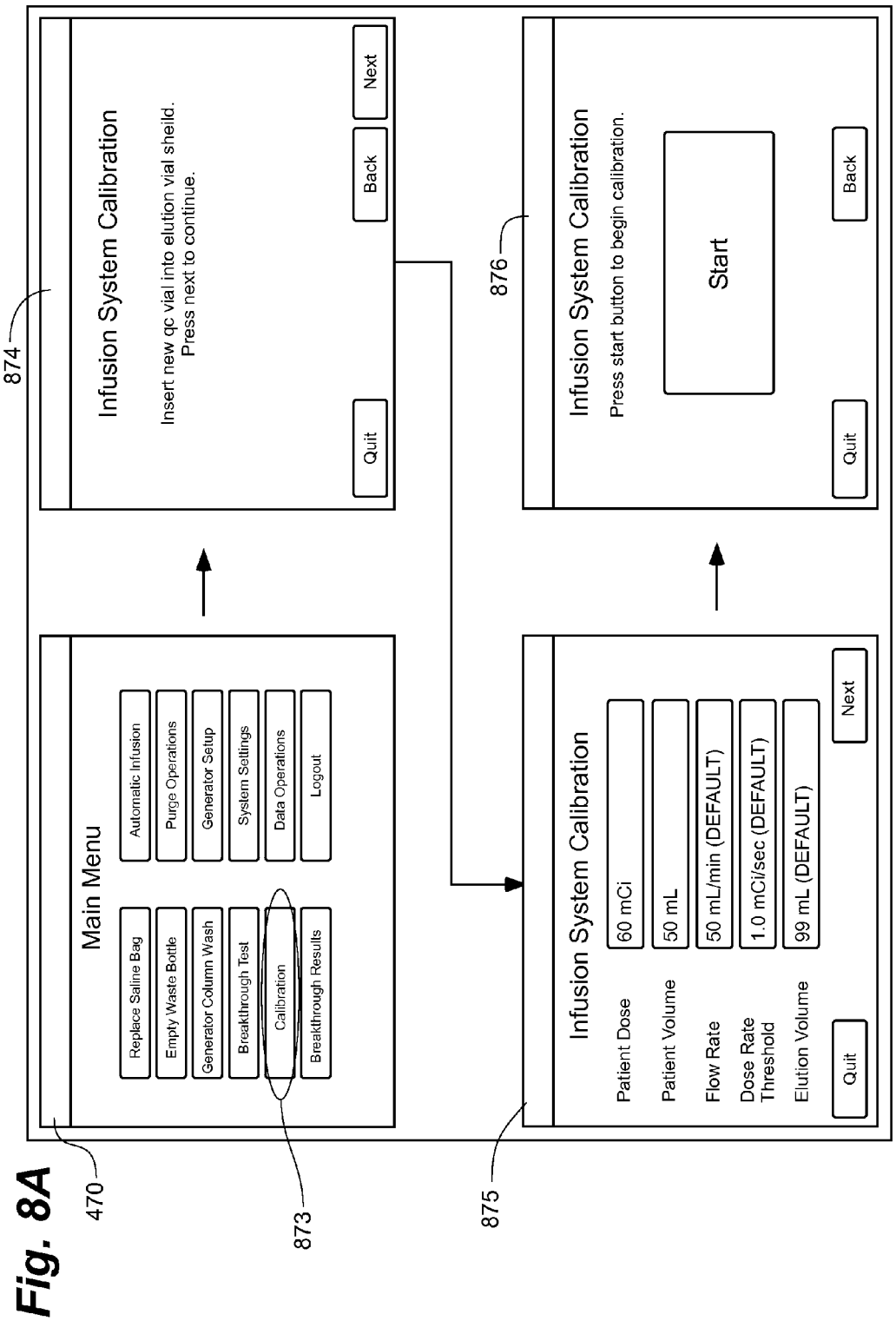
FIGS. 8A-B are schematics showing a fifth group of successive screen shots from the computer interface, according to some embodiments.

With reference to FIG. 8A, during the aforementioned 60 minute time period, while waiting to complete the breakthrough testing, the user may perform calibration by selecting item 873 from main menu 470. Upon selection of item 873, computer 17 presents a screen 874, which instructs the user to insert a new test vial into an elution vial shield. In addition to placing the vial in the shield, the user, preferably, replaces patient line 305p with a new patient line, and then attaches a needle to the end of the new patient line for insertion into the test vial, in order to collect an eluate sample therefrom. After performing these steps, the user may move to screen 875, wherein a plurality of data entry fields are presented; all or some of the fields may be filled in with pre-programmed default parameters, which the user has an option to change, if necessary. Once the user confirms entry of desired parameters for the calibration, the user may enter a command, via interaction with a subsequent screen 876, to start the calibration elution.

Figure 8B:
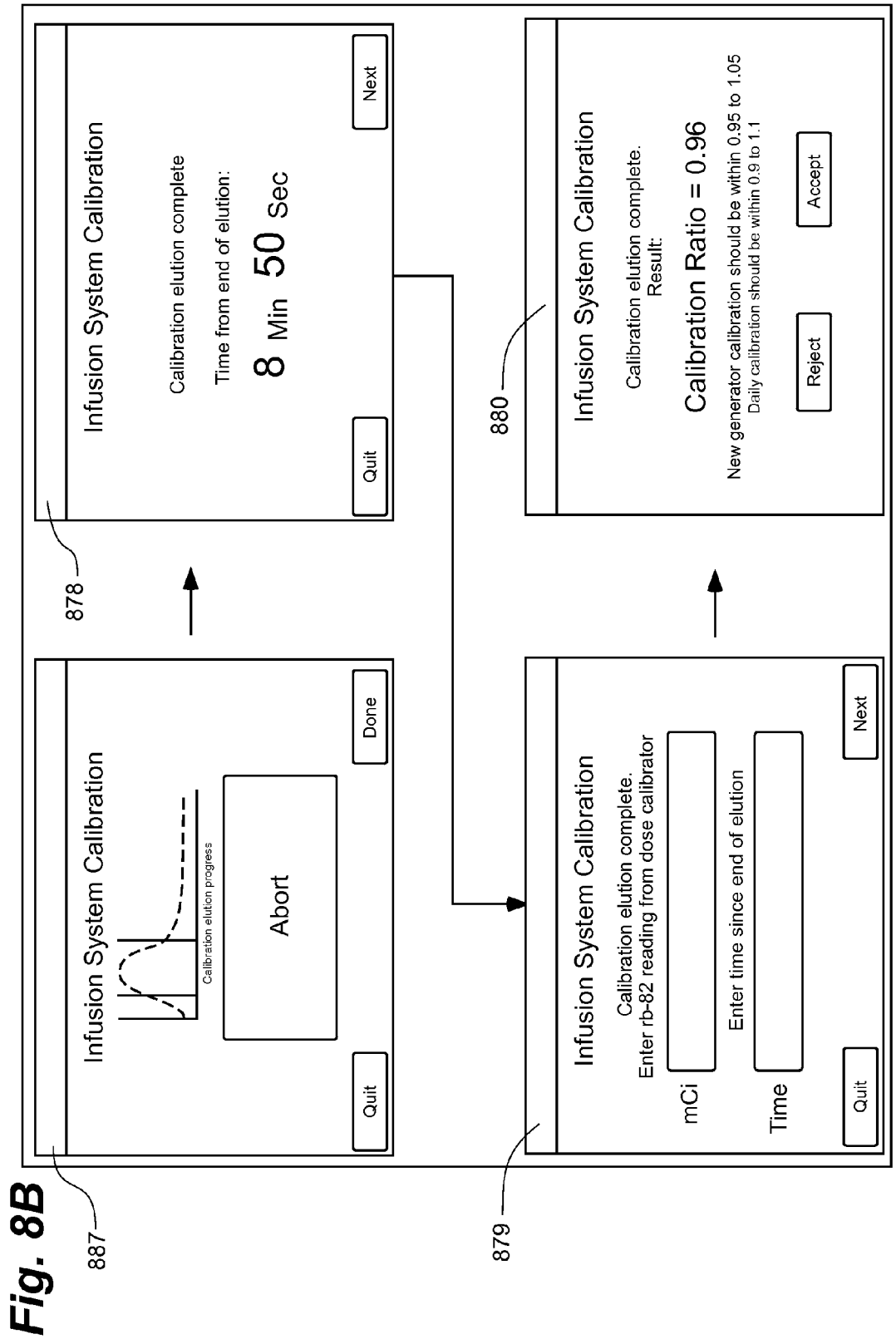

With reference to FIG. 8B, after computer 17 starts the elution process, a screen 87 informs the user that the calibration elution is in progress and provides an option to abort the elution. As previously described, the system may provide an indication that elution is in progress, for example, light projector 100 (FIG. 1C) may project a flashing light signal during that portion of the elution process when eluate is diverted from generator 21 through waste line 305w and into waste bottle 23, and then a steady light signal during that portion of the elution process when activity detector 25 has detected that a prescribed dose rate threshold is reached, for example, 1.0 mCi/sec, and the eluate is being diverted from generator 21, through the new patient line, and into the test vial. Another type of light signal, for example, the more rapidly flashing light, as previously described, may be projected when a peak bolus of radioactivity is detected in the eluate. Upon completion of the elution process for calibration, computer 17 presents a screen 878, which provides an indication of a time lapse since the completion of the elution, in terms of a time since completion of the calibration elution process. When the user transfers the vial containing the sample of eluate into the dose calibrator, to measure the activity of the sample, the user may make a note of the time lapse indicated on screen 878. With further reference to FIG. 8B, once the user has received the activity measure from the dose calibrator, the user proceeds to a screen 879, which includes data entry fields for the activity measure and the time, with respect to the completion of elution, at which the dose calibrator measured the activity of the sample. Once the data is input by the user, as described above, computer calculates a calibration coefficient, or ratio, and presents the ratio on a screen 880. According to FIG. 8B, screen 880 further provides an indication of a desirable range for the calibration ratio and presents an option for the user to reject the calculated ratio, in which case, the user may instruct computer 17 to recalculate the ratio.

Figure 9A:
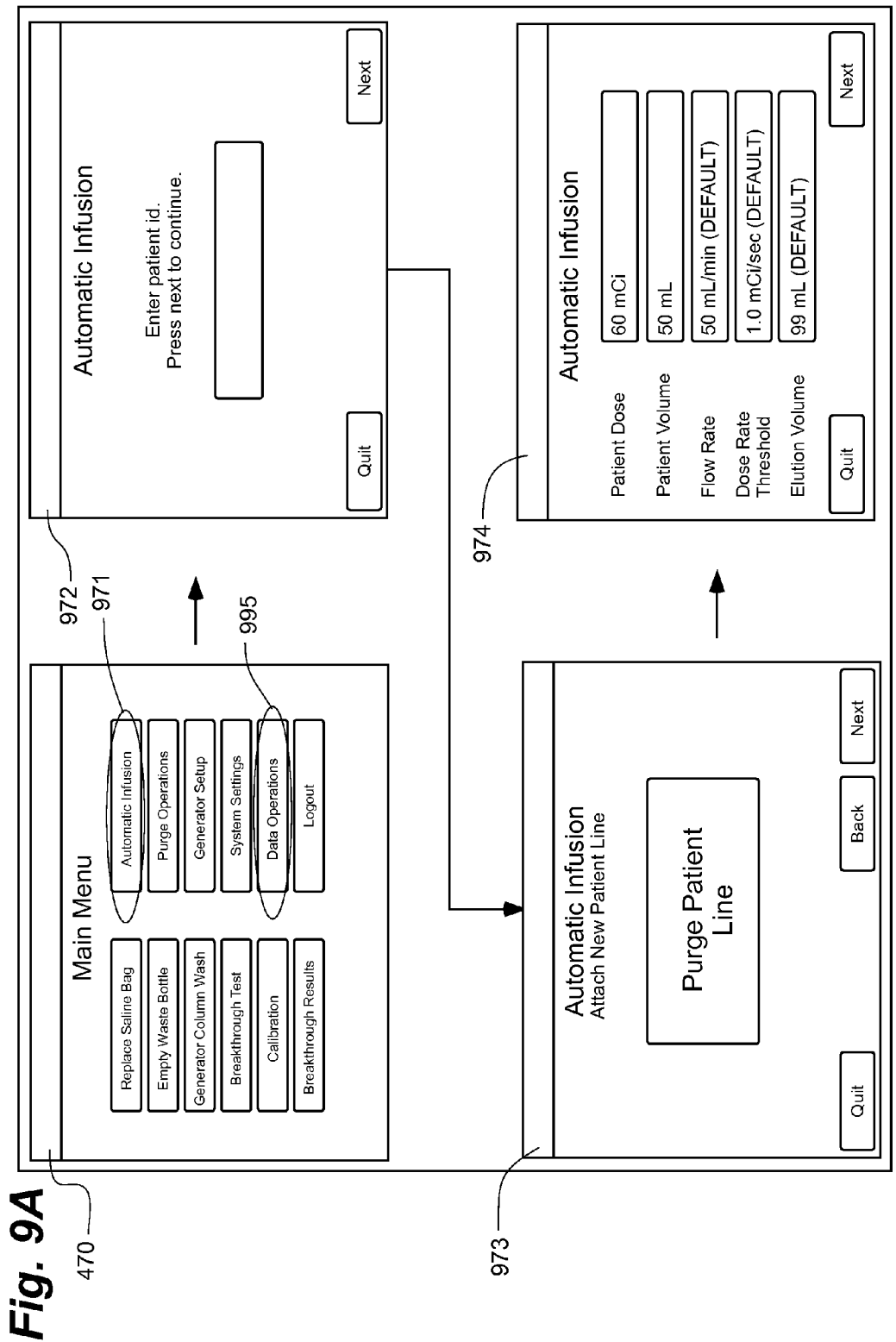

With reference to FIG. 9A, upon completion of the above-described quality control tests, the user may select an item 971, from main menu 470, in order to direct system 10 to begin a procedure for the generation and automatic infusion of a radiopharmaceutical into a patient. As previously described, system 10 infuses the patient with the radiopharmaceutical so that nuclear diagnostic imaging equipment, for example, a PET scanner, can create images of an organ of the patient, which absorbs the radiopharmaceutical, via detection of radioactive radiation therefrom. According to FIG. 9A, upon selection of item 971, computer 17 presents a screen 972 which includes a data entry field for a patient identification number. This identification number that is entered by the user is retained by computer 17, in conjunction with the pertinent system parameters associated with the patient's infusion. After the user enters the patient identification number, computer 17 directs, per a screen 973, the user to attach a new patient line and to purge the patient line of air. A subsequent screen 974 presented by computer 17 includes data entry fields by which the user may establish parameters for the automatic infusion; all or some of the fields may be filled in with pre-programmed default parameters, which the user has an option to change, if necessary.

Figure 9B:
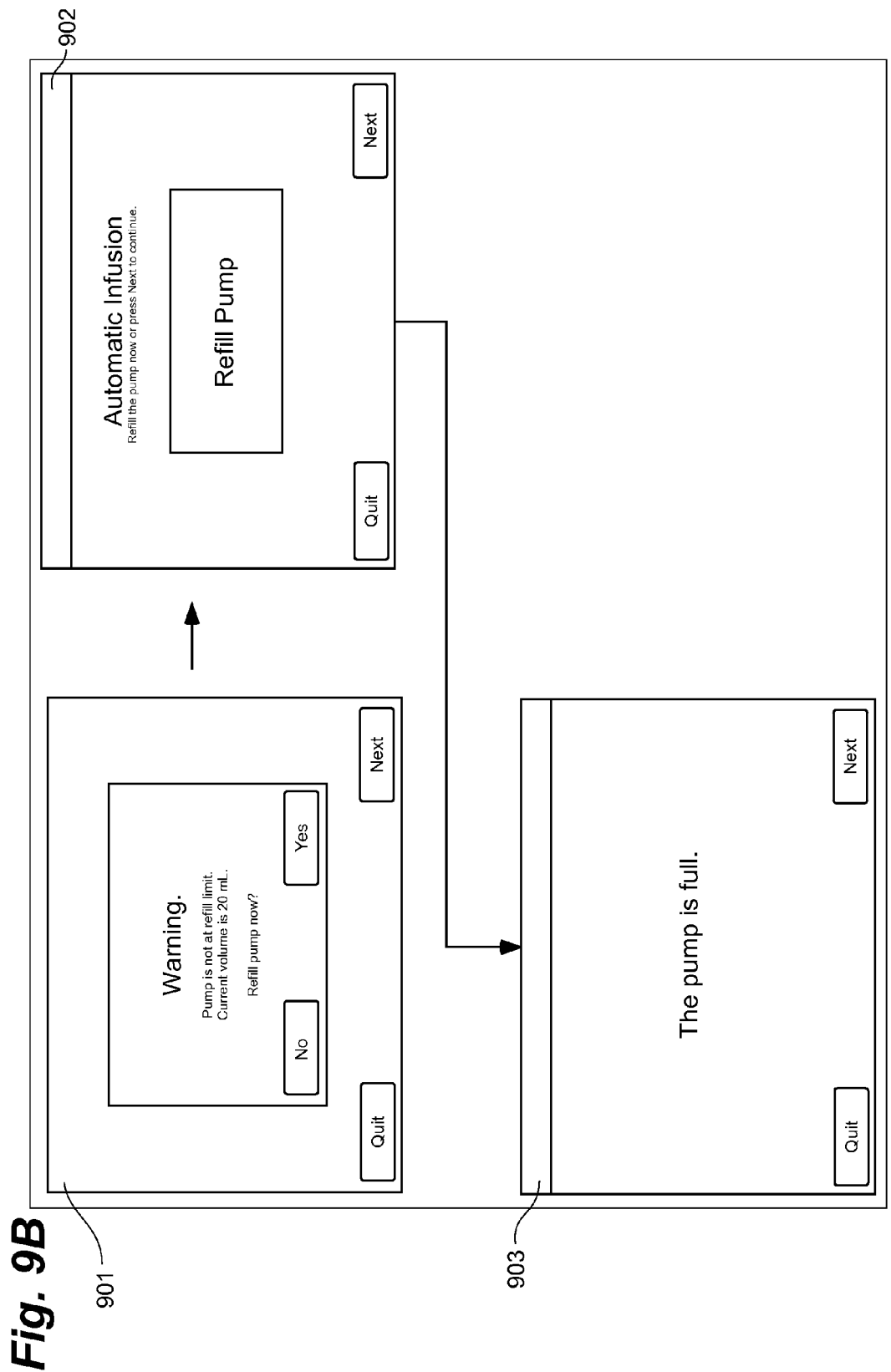

With reference to FIG. 9B, if pump 33 does not contain enough eluant/saline for the patient infusion, computer 17 will present a warning, via a screen 901, which includes an option for the user to direct the refilling of pump 33, via a subsequent screen 902. Once pump 33 has been filled, computer 17 presents an indication to the user, via a screen 903. According to some embodiments, if the user does not re-fill pump 33, yet attempts to proceed with an infusion, system 10 will preclude the infusion and present another screen, that communicates to the user that no infusion is possible, if the pump is not refilled, and asking the user to refill the pump, as in screen 901. When pump 33 contains a sufficient volume of eluant for the patient infusion, computer 17 presents a screen 975, which is shown in FIG. 9C, and allows the user to enter a command for system 10 to start the patient infusion. During the infusion, computer 17 provides the user with an indication that the infusion is in process and with an option for the user to abort the infusion, via a screen 976. As previously described, the system may provide an indication that an elution is in progress, for example, light projector 100 (FIG. 1C) may project a flashing light signal during that portion of the elution process when eluate is diverted from generator 21 through waste line 305w and into waste bottle 23, and then a steady light signal during that portion of the elution process when activity detector 25 has detected that a prescribed dose rate threshold is reached, for example, 1.0 mCi/sec, and the eluate is being diverted from generator 21, through the new patient line for infusion into the patient. Another type of light signal, for example, the more rapidly flashing light, previously described, may be projected when a peak bolus of radioactivity is detected in the eluate. At the completion of the infusion, a screen 977 is displayed by computer 17 to inform the user of the completion of the infusion and a time since the completion. Computer 17 also displays a summary of the infusion, per screen 978.

Printer 117 (FIG. 1B) may be activated to print out a hard copy of the infusion summary, on which the patient identification number and pertinent system parameters are also printed, for reference. Alternatively, or in addition, according to some embodiments, the summary of the infusion, which includes the patient identification number and pertinent system parameters, may be downloaded onto a computer readable storage device to be transferred to one or more remote computers and/or automatically transferred thereto, via wireless communication or a cable connection. The one or more remote computers may be included, for example, in a hospital information system, and/or an inventory system, and/or a billing system, and/or in a medical imaging system. With reference back to FIG. 9A the user may select an item 995, from main menu 470, in order have system 10 perform data operations, such as, archiving a data base of patient infusion information and quality control test results, transmitting patient infusion summary records to USB mass storage devices, and various types of data filtering, for example, according to date ranges and/or patient identification numbers, for example, to search for a particular set of data and/or to compile a summary report of related sets of data.

Figure 10:
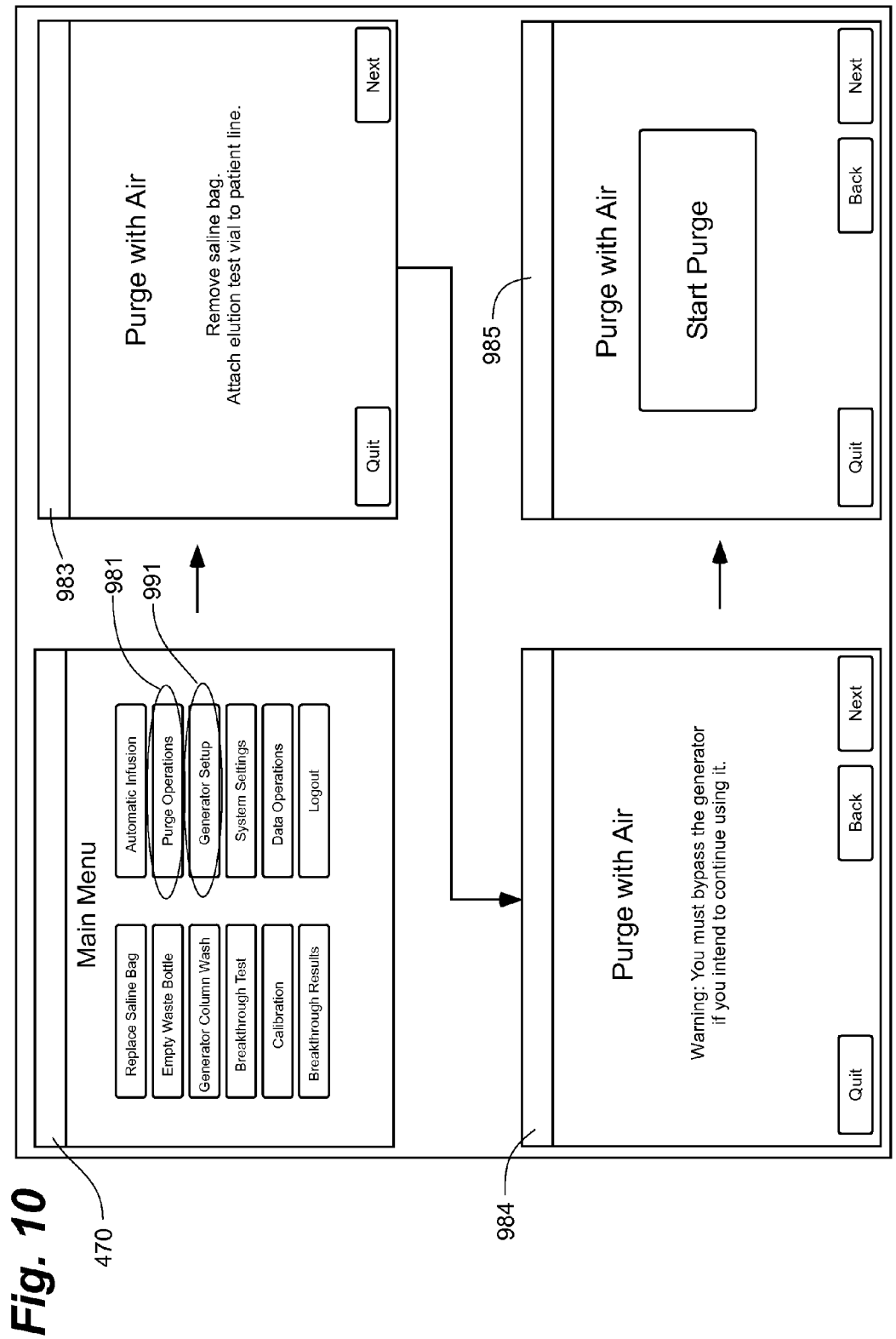
FIG. 10 is a schematic showing a seventh group of successive screen shots from the computer interface, according to some embodiments.

Turning now to FIG. 10, an item 981 for computer-facilitated purging of the tubing lines of system 10 is shown included in main menu 470. When a user selects item 981, computer 17 guides the user to select either an air purge or a saline purge. The direction provided by computer 17 is not explicitly laid out herein, for a saline purge, as procedures for saline purging should be readily apparent to those skilled in the art, with reference to the schematic of infusion circuit 300 shown in FIG. 1D. A saline purge of circuit 300 is desired to assure that all the air is removed from circuit 300 when a new generator and/or a new complete or partial tubing set is installed. An air purge of the tubing lines of circuit 300 may be performed after removing reservoir 15, by-passing generator 21, by connecting tubing line 304 to tubing line 305, and coupling patient line 305p to a vial, for example, as is directed by the computer interface, in screens 983 and 984 shown in FIG. 10. The air purge is desirable for blowing out the tubing lines, thereby removing all remaining eluant and eluate, prior to installing a new generator and/or prior to transporting system 10 from one site to another. If generator 21 is not depleted and will be used in system 10 at the new site, it is important to by-pass the generator prior to purging the tubing lines of circuit 300 with air, so that air is not blown across the generator, since air through generator 21 may compromise both the function and the aseptic nature of generator 21.

According to preferred embodiments, once the user has followed the instructions presented in screens 983 and 984 and selects to start the air purge, for example, via screen 985, computer 17 directs the controller of system 10 to carry out a complete air purge, in which pump 33 and divergence valves 35BG and 35WP are automatically controlled. The automated air purge preferably includes the following steps, which may be best understood with reference to tubing circuit 300 in FIG. 1D: pumping any remaining volume of eluant left in pump 33, through lines 302, 304, 305 and 305w, to waste bottle 23; refilling pump 33 with air and pumping the air through lines 302, 304, 305 and 305w, into waste bottle 23 (lines 304 and 305 have been previously connected directly to one another, in order to by-pass generator 21; if generator 21 is depleted and will be replaced with a new generator, pumping air through generator 21 may be acceptable); refilling pump 33 with air and then pumping a portion of the air through lines 302, 304, 305 and 305p, into the vial, and then a remaining portion of the air through lines 302, 304, 303 and 305p, into the vial. With reference to FIG. 1D and the previous description of divergence valves 35BG, 35WP, it should be understood how divergence valves 35BG, 35WP are automatically controlled to carry out the above steps.

The purge operations, which are facilitated by selecting item 981 from main menu 470, may also be accessed via the selection of an item 991 for generator setup. When the user selects item 991, computer 17 may present an option for guidance in removing an old, depleted, generator and a set of tubing lines, prior to installing the new generator, or an option to just be guided in the installation of the new generator.

In the foregoing detailed description, the invention has been described with reference to specific embodiments. However, it may be appreciated that various modifications and changes can be made without departing from the scope of the invention as set forth in the appended claims.

We claim:

1. A shielding assembly for an infusion system, the shielding assembly being mounted within a cabinet structure, and the shielding assembly comprising:
   a plurality of compartments having sidewalls providing barriers to radioactive radiation for the compartments;
   a corresponding plurality of doors, each door, when open, providing access to the corresponding compartment via an opening in its sidewall, and, when closed, providing further barrier to radioactive radiation for the corresponding compartment;
   a first compartment of the plurality of compartments enclosed by a first sidewall of the sidewalls and sized to contain a radioisotope generator of the infusion system, the first sidewall including a first sidewall opening oriented upward and aligned with a first upper opening through a shell of the cabinet structure, an upper surface of the shell being located at an elevation with respect to a lowermost portion of the cabinet structure substantially greater than the first sidewall opening and the first upper opening.

2. The shielding assembly of claim 1, wherein the lowermost portion of the cabinet structure is at approximately ground level, the first sidewall opening is at an elevation of between approximately 12 inches and approximately 24 inches with respect to the lowermost portion of the cabinet.

3. The shielding assembly of claim 2, wherein the upper surface of the shell is at an elevation of between approximately 24 inches and 36 inches with respect to the lowermost portion of the cabinet structure.

4. The shielding assembly of claim 1, further comprising a second compartment of the plurality of compartments enclosed by a second sidewall of the sidewalls and sized to contain a waste bottle of the infusion system, the second sidewall including a second sidewall opening oriented upward and aligned with a second upper opening through the shell of the cabinet structure, the second upper opening being an opening in the upper surface of the shell.

5. A shielding assembly for an infusion system, the shielding assembly being mounted within a cabinet structure, and the shielding assembly comprising:
a first compartment sized to contain a radioisotope generator of the infusion system, the first compartment being enclosed by a first sidewall that forms a barrier to radioactive radiation, the first sidewall including an opening extending therethrough and a lid, the lid mating with the opening to alternately enclose the first compartment and provide access to the first compartment, via the opening, and the opening being oriented upward and located at a first elevation with respect to a lowermost portion of the cabinet structure;
a second compartment sized to contain a portion of an infusion tubing circuit of the infusion system that is downstream of the generator, the second compartment being enclosed by a second sidewall that forms a barrier to radioactive radiation, the second sidewall including a base portion and a lid portion, the lid portion mating with the base portion to alternately enclose the second compartment and provide access to the second compartment; and
a third compartment sized to contain a waste bottle of the infusion system, the third compartment being enclosed by a third sidewall that forms a barrier to radioactive radiation, the third sidewall including an opening, extending through the third sidewall, and a lid, the lid of the third sidewall mating with the opening of the third sidewall to alternately enclose the third compartment and provide access to the third compartment, via the opening of the third sidewall, the opening of the third sidewall being oriented upward and located at a second elevation with respect to the lowermost portion of the cabinet structure, and the second elevation being greater than the first elevation of the opening of the first sidewall.

6. The shielding assembly of claim 5, wherein the opening of the first sidewall is aligned with a first upper opening through a shell of the cabinet structure and the opening of the third sidewall is aligned with a second upper opening through the shell of the cabinet structure, the second upper opening being located at a greater elevation with respect to the lowermost portion of the cabinet structure than the first upper opening.

7. The shielding assembly of claim 5, wherein an opening through a shell of the cabinet structure provides access to both the lid of the first sidewall and to the lid portion of the second sidewall.

8. The shielding assembly of claim 5, wherein the lowermost portion of the cabinet structure is at approximately ground level and the first elevation is between approximately 12 inches and approximately 24 inches.

9. The shielding assembly of claim 5, wherein the lowermost portion of the cabinet structure is at approximately ground level and the second elevation is between approximately 24 inches and approximately 36 inches.

10. The shielding assembly of claim 5, further comprising:
a fourth compartment sized to contain another portion of the infusion tubing circuit of the infusion system downstream from the generator, the fourth compartment being enclosed by a portion of the third sidewall and a door that forms a barrier to radioactive radiation, the door mating with the portion of the third sidewall to alternately enclose the fourth compartment and provide access to the fourth compartment; and
wherein the fourth compartment is immediately adjacent to the second compartment;
the portion of the infusion tubing circuit contained in the second compartment includes an eluate line, extending from the generator, a patient line, being coupled to the eluate line, and a waste line, being coupled to the eluate line; and
the other portion of the infusion tubing circuit contained in the fourth compartment includes an extension of the patient line, from the second compartment, and an extension of the waste line, from the second compartment.

11. The shielding assembly of claim 10, wherein the fourth compartment extends approximately vertically along the portion of the third sidewall, on an opposite side of the third sidewall from the third compartment.

12. The shielding assembly of claim 11, wherein the fourth compartment includes a retaining member to hold the extension of the patient line and the extension of the waste line in place within the fourth compartment.

13. The shielding assembly of claim 10, wherein the lid of the third sidewall, when mated with opening of the third sidewall, prevents the door of the fourth compartment from opening to provide access to the fourth compartment.

14. The shielding assembly of claim 13, wherein the door of the fourth compartment, when mated with the portion of the third sidewall, prevents the lid portion of the second sidewall from opening to provide access to the second compartment.

15. The shielding assembly of claim 14, wherein the lid portion of the second sidewall, when mated with the base portion of the second sidewall, prevents the lid of the first sidewall from opening to provide access to the first compartment.

16. The shielding assembly of claim 10, wherein the door of the fourth compartment, when mated with the portion of the third sidewall, prevents the lid portion of the second sidewall from opening to provide access to the second compartment.

17. The shielding assembly of claim 5, wherein the lid portion of the second sidewall, when mated with the base portion of the second sidewall, prevents the lid of the first sidewall from opening to provide access to the first compartment.

18. The shielding assembly of claim 5, wherein the lid of the first sidewall is hinged to open in an upward direction; and further comprising a latch component, mounted within the cabinet structure, to hold the lid of the first sidewall in an open position.

19. The shielding assembly of claim 5, wherein the lid portion of the second sidewall is hinged to open in an upward direction; and further comprising a latch component, mounted within the cabinet structure, to hold the lid portion of the second sidewall in an open position.

20. A method for setting up an infusion system, the method comprising:
opening a first door of a shielding assembly of the infusion system to access a first compartment of the assembly and to allow for a second door of the shielding assembly to be opened, wherein the first door defines a first door edge, the second door defines a second door edge, and the first door edge overlaps the second door edge so as to prevent the second door from being opened if the first door is not open; and opening the second door, after opening the first door, to access a second compartment of the shielding assembly, the second compartment being separate from, and outside of, the first compartment;

placing a radioisotope generator into the second compartment and connecting the generator to an infusion tubing circuit;

placing a portion of the infusion tubing circuit into the first compartment;

closing the second door to enclose the generator within the second compartment; and closing the first door, after closing the second door, to enclose the portion of the infusion tubing circuit within the first compartment.

21. The method of claim 20, further comprising unlocking and removing an access panel from a shell of a cabinet structure, which encloses the shielding assembly, to access the first door and the second door of the shielding assembly.

22. The method of claim 20, further comprising:
opening a third door, prior to opening the first door, to access a third compartment of the shielding assembly and to allow for the first door to be opened;
placing another portion of the infusion tubing circuit into the third compartment; and
closing the third door, after closing the first door, to enclose the other portion of the infusion tubing circuit within the third compartment.

23. The method of claim 22, further comprising unlocking and removing an access panel from a shell of a cabinet structure, which encloses the shielding assembly, to access the first door, the second door and the third door of the shielding assembly.

24. The method of claim 22, further comprising:
opening a fourth door, prior to opening the third door, to access a fourth compartment of the shielding assembly and to allow for the third door to be opened;
connecting a waste line of the infusion tubing circuit to a waste bottle;
placing the waste bottle into the fourth compartment; and
closing the fourth door, after closing the third door, to enclose the waste bottle within the fourth compartment.

25. The method of claim 20, further comprising securing at least one of the first and second doors in an open position.

26. A shielding assembly for an infusion system, the shielding assembly comprising a plurality of compartments and providing a radioactive radiation barrier for the compartments, the assembly further comprising:
a first door to alternately enclose and provide access to a first compartment of the plurality of compartments, the first compartment sized to contain a radioisotope generator of the infusion system; and
a second door to alternately enclose and provide access to a second compartment of the plurality of compartments, the second compartment being separate from, and outside of, the first compartment, the second compartment being sized to contain a portion of an infusion tubing circuit of the infusion system that is downstream of the generator, and the second door, when enclosing the second compartment, preventing the first door from opening to provide access to the first compartment,
wherein the first door defines a first door edge, the second door defines a second door edge, and the first door edge overlaps the second door edge so as to prevent the first door from being opened if the second door is not open.

27. The shielding assembly of claim 26, further comprising a third door to alternately enclose and provide access to a third compartment of the plurality of compartments, the third compartment sized to contain another portion of the infusion tubing circuit of the infusion system downstream from the generator, the third door, when enclosing the third compartment, preventing the second door from opening to provide access to the second compartment.

28. The shielding assembly of claim 27, further comprising a fourth door to alternately enclose and provide access to a fourth compartment of the plurality of compartments, the fourth compartment being sized to contain a waste bottle of the infusion system, the fourth door, when enclosing the fourth compartment, preventing the third door from opening to provide access to the third compartment.

29. The shielding assembly of claim 28, wherein the third compartment shares a sidewall with the fourth compartment and extends approximately vertically along the shared sidewall.

30. The shielding assembly of claim 29, wherein the third compartment includes a retaining member attached to the shared sidewall to hold the other portion of the infusion tubing circuit in place along the shared sidewall.

31. An infusion system comprising:
a cabinet structure including a shell defining an interior space thereof, the shell including a first opening, a second opening and an access panel, the access panel mating with the second opening and being removable therefrom;
a lock reversibly engaging the access panel to secure access to the interior space of the cabinet structure;
an eluant source;
a shielding assembly located within the interior space of the cabinet structure, the shielding assembly including a sidewall defining a plurality of compartments and providing a barrier to radioactive radiation for the compartments, the shielding assembly further including a corresponding plurality of doors, each door, when open, providing access to the corresponding compartment via an opening in the sidewall, and, when closed, providing further barrier to radioactive radiation for the corresponding compartment;
a radioisotope generator contained within a first compartment of the plurality of compartments of the shielding assembly and being accessible through the second opening of the shell of the cabinet structure, when the access panel is unlocked, and when a first door of the plurality of doors, which corresponds to the first compartment, is open;
an eluant line coupled to the eluant source and to the generator;
an eluate line coupled to the generator; and
a patient line coupled to the eluate line and extending out from the interior space of the cabinet structure through the first opening of the shell.

32. The assembly of claim 31, wherein the first door is hinged to open in an upward direction; and further comprising a latch component, mounted within the cabinet structure, to hold the first door in an open position.

33. The system of claim 31, further comprising:
a waste bottle contained within a second compartment of the plurality of compartments of the shielding assembly; and
a waste line coupled to the eluate line and to the waste bottle;

wherein the shell of the cabinet structure further includes a third opening; and a second door of the plurality of doors, which corresponds to the second compartment, is aligned with the third opening of the shell, for access thereto, and is located at a higher elevation, with respect to a lowermost surface of the cabinet structure, than that of the second door.

34. The system of claim 31, further comprising:
a waste bottle contained within a second compartment of the plurality of compartments of the shielding assembly; and
a waste line coupled to the eluate line and to the waste bottle;
wherein a second door of the plurality of doors, which corresponds to the second compartment, when closed, prevents the first door from opening to provide access to the first compartment.

35. The system of claim 31, wherein:
the eluate line and at least a portion of the patient line are contained in a second compartment of the plurality of compartments of the shielding assembly; and
a second door of the plurality of doors, which corresponds to the second compartment, when closed, prevents the first door from opening to provide access to the first compartment.

36. The system of claim 35, wherein the second door is accessible only through the second opening of the shell of the cabinet structure, when the access panel is unlocked.

37. The system of claim 35, wherein the first door and the second door are both hinged to open in an upward direction; and further comprising at least one latch component, mounted within the cabinet structure, to hold the first door and the second door in an open position.

* * * * *